United States Patent
Petkovich et al.

(10) Patent No.: US 11,752,158 B2
(45) Date of Patent: Sep. 12, 2023

(54) METHOD OF TREATING VITAMIN D INSUFFICIENCY AND DEFICIENCY

(75) Inventors: P. Martin Petkovich, Kingston (CA); Christian F. Helvig, Markham (CA); Samir P. Tabash, Whitby (CA)

(73) Assignee: EIRGEN PHARMA LTD., Waterford (IE)

( * ) Notice: Subject to any disclaimer, the term of this patent is extended or adjusted under 35 U.S.C. 154(b) by 0 days.

(21) Appl. No.: 12/597,230

(22) PCT Filed: Apr. 25, 2008

(86) PCT No.: PCT/IB2008/003480
§ 371 (c)(1),
(2), (4) Date: Dec. 24, 2009

(87) PCT Pub. No.: WO2009/047644
PCT Pub. Date: Apr. 16, 2009

(65) Prior Publication Data
US 2010/0120728 A1    May 13, 2010

Related U.S. Application Data

(60) Provisional application No. 60/913,849, filed on Apr. 25, 2007.

(51) Int. Cl.
*A61K 31/592* (2006.01)
*A61K 31/593* (2006.01)

(52) U.S. Cl.
CPC .......... *A61K 31/592* (2013.01); *A61K 31/593* (2013.01)

(58) Field of Classification Search
CPC .............. A61K 2300/00; A61K 31/592; A61K 31/593; A61K 9/4858; A61P 3/02
USPC .................................. 514/167, 157; 552/653
See application file for complete search history.

(56) References Cited

U.S. PATENT DOCUMENTS

| | | |
|---|---|---|
| 3,565,924 A | 2/1971 | DeLuca et al. |
| 3,833,622 A | 9/1974 | Babcock et al. |
| 3,880,894 A | 4/1975 | De Luca et al. |
| 3,974,272 A | 8/1976 | Polli et al. |
| 4,004,003 A | 1/1977 | Babcock et al. |
| 4,230,701 A | 10/1980 | Holick et al. |
| 4,335,120 A | 6/1982 | Holick et al. |
| 4,442,093 A | 4/1984 | Maeda et al. |
| 4,448,721 A | 5/1984 | Deluca et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 4,892,821 A | 1/1990 | Omura et al. |
| 4,997,824 A | 3/1991 | Popovtzer et al. |
| 5,026,559 A | 6/1991 | Eichel et al. |
| 5,160,742 A | 11/1992 | Mazer et al. |
| 5,167,965 A | 12/1992 | Schulz |
| 5,328,903 A | 7/1994 | Ishii et al. |
| 5,342,626 A | 8/1994 | Winston et al. |
| 5,354,743 A | 10/1994 | Thys-Jacobs |
| 5,403,831 A * | 4/1995 | DeLuca et al. ............... 514/167 |
| 5,431,917 A | 7/1995 | Yamamoto et al. |
| 5,472,712 A | 12/1995 | Oshlack et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,756,123 A | 5/1998 | Yamamoto et al. |
| 5,783,215 A | 7/1998 | Arwidsson et al. |
| 5,795,882 A | 8/1998 | Bishop et al. |
| 5,861,386 A | 1/1999 | Knutson et al. |
| 5,869,473 A | 2/1999 | Knutson et al. |
| 5,872,113 A | 2/1999 | Nestor et al. |
| 5,888,994 A | 3/1999 | Hennessy et al. |
| 5,919,986 A | 7/1999 | Barbier et al. |
| 5,939,408 A | 8/1999 | Batcho et al. |
| 5,958,451 A | 9/1999 | Chen |
| 5,976,784 A * | 11/1999 | DeLuca et al. ................... 435/4 |
| 6,001,884 A | 12/1999 | Nemeth et al. |
| 6,011,068 A | 1/2000 | Nemeth et al. |
| 6,031,003 A | 2/2000 | Nemeth et al. |
| 6,034,075 A | 3/2000 | Thys-Jacobs |
| 6,051,567 A | 4/2000 | Abrahamson et al. |
| 6,096,876 A | 8/2000 | St-Arnaud et al. |
| 6,121,469 A | 9/2000 | Norman et al. |
| 6,133,250 A * | 10/2000 | Knutson et al. .............. 514/167 |
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | van Lengerich |
| 6,190,695 B1 | 2/2001 | Hoshino et al. |
| 6,211,244 B1 | 4/2001 | Van et al. |

(Continued)

FOREIGN PATENT DOCUMENTS

| | | |
|---|---|---|
| CA | 2241205 A1 | 7/1997 |
| CN | 101668517 A | 3/2010 |

(Continued)

OTHER PUBLICATIONS

Michael Holick, Journal of Cellular Biochemistry. 88:296-307 (2003).*

(Continued)

*Primary Examiner* — James D. Anderson
(74) *Attorney, Agent, or Firm* — MARSHALL, GERSTEIN & BORUN LLP

(57) ABSTRACT

The invention relates to methods and compositions for reducing toxicity associated with administration of vitamin D3, its 25-hydroxylated and 1-hydroxylated forms, and analogs thereof.

19 Claims, 6 Drawing Sheets

(56) References Cited

U.S. PATENT DOCUMENTS

| | | |
|---|---|---|
| 6,214,376 B1 | 4/2001 | Gennadios |
| 6,228,849 B1 | 5/2001 | Thys-Jacobs |
| 6,242,434 B1 | 6/2001 | Bishop et al. |
| 6,265,392 B1 | 7/2001 | Abrahamson et al. |
| 6,274,169 B1 | 8/2001 | Abrahamson et al. |
| 6,288,849 B1 | 9/2001 | Teramoto |
| 6,313,146 B1 | 11/2001 | Van et al. |
| 6,340,473 B1 | 1/2002 | Tanner et al. |
| 6,342,249 B1 | 1/2002 | Wong et al. |
| 6,375,981 B1 | 4/2002 | Gilleland et al. |
| 6,376,479 B1 | 4/2002 | Knutson et al. |
| 6,380,408 B1 | 4/2002 | Posner et al. |
| 6,413,463 B1 | 7/2002 | Yamamoto et al. |
| 6,432,936 B1 | 8/2002 | DeLuca et al. |
| 6,491,950 B1 | 12/2002 | Gutierrez-Rocca et al. |
| 6,503,893 B2 | 1/2003 | Bishop et al. |
| 6,521,608 B1 | 2/2003 | Henner et al. |
| 6,524,788 B1 | 2/2003 | Cantor |
| 6,569,463 B2 | 5/2003 | Patel et al. |
| 6,572,888 B2 | 6/2003 | Byrd |
| 6,582,727 B2 | 6/2003 | Tanner et al. |
| 6,596,314 B2 | 7/2003 | Wong et al. |
| 6,627,622 B2 * | 9/2003 | DeLuca et al. ............... 514/167 |
| 6,645,527 B2 | 11/2003 | Oshlack et al. |
| 6,770,295 B1 | 8/2004 | Kreilgaard et al. |
| 6,887,493 B2 | 5/2005 | Shefer et al. |
| 6,893,658 B1 | 5/2005 | Iida et al. |
| 6,903,083 B2 | 6/2005 | Knutson et al. |
| 6,911,217 B1 | 6/2005 | Gren et al. |
| 6,923,988 B2 | 8/2005 | Patel et al. |
| 6,929,803 B2 | 8/2005 | Wong et al. |
| 6,949,256 B2 | 9/2005 | Fonkwe et al. |
| 6,982,258 B2 | 1/2006 | Posner et al. |
| RE39,079 E | 4/2006 | Tanner et al. |
| 7,033,996 B2 | 4/2006 | Christakos |
| 7,056,655 B2 | 6/2006 | Cantor |
| 7,101,865 B2 | 9/2006 | Posner et al. |
| 7,122,530 B2 | 10/2006 | Bishop et al. |
| 7,166,585 B2 | 1/2007 | Posner et al. |
| 7,189,843 B2 | 3/2007 | Tsai et al. |
| 7,226,932 B2 | 6/2007 | Gokhale et al. |
| 7,255,921 B2 | 8/2007 | Kamaguchi et al. |
| 7,422,758 B2 | 9/2008 | Block et al. |
| 7,528,122 B2 * | 5/2009 | DeLuca et al. ............... 514/167 |
| 7,632,518 B2 | 12/2009 | Tritsch et al. |
| 7,648,826 B1 | 1/2010 | Albertson et al. |
| 7,807,194 B2 | 10/2010 | Modliszewski et al. |
| 7,816,341 B2 | 10/2010 | Sewall et al. |
| 7,829,595 B2 | 11/2010 | Lawrence et al. |
| 7,846,475 B2 | 12/2010 | Shiraishi et al. |
| 7,973,024 B2 | 7/2011 | Posner et al. |
| 8,088,410 B2 | 1/2012 | Tritsch et al. |
| 8,101,203 B2 | 1/2012 | Cao |
| 8,101,204 B2 | 1/2012 | Cao |
| 8,142,811 B2 | 3/2012 | Oshlack et al. |
| 8,207,149 B2 * | 6/2012 | Tabash ............... A61K 9/4866 514/167 |
| 8,231,896 B2 | 7/2012 | Tanner et al. |
| 8,268,352 B2 | 9/2012 | Vaya et al. |
| 8,293,270 B2 | 10/2012 | Sukuru |
| 8,329,677 B2 | 12/2012 | Bishop et al. |
| 8,361,488 B2 * | 1/2013 | Bishop et al. ............... 424/422 |
| 8,377,470 B2 | 2/2013 | Tanner et al. |
| 8,426,391 B2 * | 4/2013 | Bishop et al. ............... 514/167 |
| 8,592,401 B2 | 11/2013 | Petkovich et al. |
| 8,759,328 B2 | 6/2014 | Deluca et al. |
| 8,778,373 B2 * | 7/2014 | Bishop et al. ............... 424/422 |
| 8,906,410 B2 | 12/2014 | Bishop et al. |
| 8,962,239 B2 | 2/2015 | Petkovich et al. |
| 8,992,971 B2 | 3/2015 | Yang |
| 9,017,720 B2 | 4/2015 | Andersen et al. |
| 9,125,823 B2 | 9/2015 | Selva et al. |
| 9,402,855 B2 | 8/2016 | Bishop et al. |
| 9,408,858 B2 | 8/2016 | Bishop et al. |
| 9,498,486 B1 | 11/2016 | Bishop et al. |
| 9,500,661 B2 | 11/2016 | Petkovich et al. |
| 9,913,852 B2 | 3/2018 | Bishop et al. |
| 10,220,047 B2 | 3/2019 | Petkovich et al. |
| 2001/0028896 A1 | 10/2001 | Byrd |
| 2001/0036472 A1 | 11/2001 | Wong et al. |
| 2002/0018810 A1 | 2/2002 | Oshlack et al. |
| 2002/0031798 A1 | 3/2002 | Anazawa et al. |
| 2002/0044968 A1 | 4/2002 | Van Lengerich |
| 2002/0081331 A1 | 6/2002 | Tanner et al. |
| 2002/0128240 A1 | 9/2002 | Mazess |
| 2002/0155154 A1 | 10/2002 | Wong et al. |
| 2002/0183288 A1 | 12/2002 | Mazess et al. |
| 2003/0059471 A1 | 3/2003 | Compton et al. |
| 2003/0083360 A1 | 5/2003 | Crotts et al. |
| 2003/0129194 A1 | 7/2003 | Mazess et al. |
| 2003/0138482 A1 | 7/2003 | Fonkwe et al. |
| 2003/0152629 A1 | 8/2003 | Shefer et al. |
| 2003/0157560 A1 | 8/2003 | Cantor |
| 2003/0191093 A1 | 10/2003 | Chen et al. |
| 2003/0195171 A1 * | 10/2003 | Daifotis ............... A61K 31/59 514/89 |
| 2004/0043971 A1 | 3/2004 | Mazess et al. |
| 2004/0092534 A1 | 5/2004 | Yam et al. |
| 2004/0101554 A1 | 5/2004 | Kirschner et al. |
| 2004/0132695 A1 | 7/2004 | Posner et al. |
| 2004/0197407 A1 | 10/2004 | Subramanian et al. |
| 2004/0224930 A1 | 11/2004 | Posner et al. |
| 2004/0258749 A1 | 12/2004 | Guldner et al. |
| 2005/0014211 A1 | 1/2005 | Armbruster et al. |
| 2005/0019374 A1 | 1/2005 | Modliszewski et al. |
| 2005/0037064 A1 | 2/2005 | Basquin et al. |
| 2005/0069579 A1 | 3/2005 | Kamaguchi et al. |
| 2005/0101576 A1 | 5/2005 | Whitehouse et al. |
| 2005/0106233 A1 | 5/2005 | Andersen et al. |
| 2005/0124591 A1 | 6/2005 | Tian et al. |
| 2005/0143358 A1 | 6/2005 | Deluca et al. |
| 2005/0147669 A1 | 7/2005 | Lawrence et al. |
| 2005/0148557 A1 | 7/2005 | Tian et al. |
| 2005/0148558 A1 | 7/2005 | Knutson et al. |
| 2005/0186268 A1 | 8/2005 | Hoshi et al. |
| 2005/0208055 A1 | 9/2005 | Chuang et al. |
| 2005/0287213 A1 | 12/2005 | Wong et al. |
| 2006/0009425 A1 | 1/2006 | Delgado-Herrera et al. |
| 2006/0019933 A1 | 1/2006 | Boardman et al. |
| 2006/0029660 A1 | 2/2006 | Fonkwe et al. |
| 2006/0034937 A1 | 2/2006 | Patel |
| 2006/0057201 A1 | 3/2006 | Bonney et al. |
| 2006/0193877 A1 | 8/2006 | Tengler et al. |
| 2006/0210610 A1 | 9/2006 | Davidson et al. |
| 2006/0223119 A1 | 10/2006 | Cantor |
| 2006/0228808 A1 | 10/2006 | Clarke et al. |
| 2006/0257481 A1 | 11/2006 | Gurney et al. |
| 2007/0026067 A1 | 2/2007 | Yam et al. |
| 2007/0027120 A1 | 2/2007 | Whitehouse et al. |
| 2007/0032461 A1 | 2/2007 | Adorini et al. |
| 2007/0122477 A1 * | 5/2007 | Bishop ............... A61K 9/4841 424/468 |
| 2007/0155664 A1 | 7/2007 | Ranklove et al. |
| 2007/0190146 A1 | 8/2007 | Roger et al. |
| 2007/0207488 A1 | 9/2007 | Trump et al. |
| 2008/0109983 A1 | 5/2008 | Davis |
| 2008/0134937 A1 | 6/2008 | Yang |
| 2008/0199534 A1 | 8/2008 | Goldberg et al. |
| 2008/0317764 A1 | 12/2008 | Huber et al. |
| 2009/0004284 A1 | 1/2009 | Cheng et al. |
| 2009/0069389 A1 | 3/2009 | Choi et al. |
| 2009/0137536 A1 | 5/2009 | Mazess et al. |
| 2009/0155355 A1 | 6/2009 | Heuer et al. |
| 2009/0176748 A1 | 7/2009 | Tabash et al. |
| 2009/0209501 A1 | 8/2009 | Bishop et al. |
| 2009/0262685 A1 | 10/2009 | Schuringa et al. |
| 2009/0311316 A1 * | 12/2009 | Bishop et al. ............... 424/456 |
| 2010/0120728 A1 | 5/2010 | Petkovich et al. |
| 2010/0144684 A1 | 6/2010 | Bishop |
| 2010/0204189 A1 | 8/2010 | Petkovich et al. |
| 2010/0227889 A1 | 9/2010 | Gerspacher et al. |
| 2010/0291191 A1 | 11/2010 | Shoichet et al. |
| 2010/0291197 A1 | 11/2010 | Schwab |
| 2011/0039809 A1 | 2/2011 | Buck et al. |

(56) References Cited

U.S. PATENT DOCUMENTS

| | | |
|---|---|---|
| 2011/0039810 A1 | 2/2011 | Buck et al. |
| 2011/0039811 A1 | 2/2011 | Buck et al. |
| 2011/0105444 A1 | 5/2011 | Deluca et al. |
| 2011/0118218 A1* | 5/2011 | Buck .................. A23L 33/155 |
| | | 514/168 |
| 2011/0130370 A1 | 6/2011 | Briault et al. |
| 2011/0171298 A1 | 7/2011 | Cao |
| 2011/0182986 A1 | 7/2011 | Speirs et al. |
| 2011/0256230 A1 | 10/2011 | Haeusler et al. |
| 2011/0300210 A1 | 12/2011 | Swanson et al. |
| 2011/0318321 A1 | 12/2011 | Selva et al. |
| 2011/0319503 A1 | 12/2011 | Muller et al. |
| 2012/0015916 A1 | 1/2012 | Tabash et al. |
| 2012/0135103 A1 | 5/2012 | Walsh et al. |
| 2013/0085121 A1 | 4/2013 | Wang et al. |
| 2013/0137663 A1 | 5/2013 | Messner et al. |
| 2013/0178451 A1 | 7/2013 | Bishop et al. |
| 2013/0189522 A1* | 7/2013 | Fujii .................. A23P 20/105 |
| | | 428/403 |
| 2013/0216618 A1 | 8/2013 | Muller et al. |
| 2013/0302309 A1 | 11/2013 | Yang |
| 2014/0088202 A1 | 3/2014 | Cade et al. |
| 2014/0248400 A1 | 9/2014 | Phonchareon et al. |
| 2014/0274977 A1 | 9/2014 | Bishop et al. |
| 2014/0349979 A1 | 11/2014 | White et al. |
| 2014/0357603 A1 | 12/2014 | Bishop et al. |
| 2015/0079165 A1 | 3/2015 | Bishop et al. |
| 2015/0119472 A1 | 4/2015 | Shuai et al. |
| 2015/0119473 A1 | 4/2015 | Shuai et al. |
| 2017/0119677 A1 | 5/2017 | Bishop et al. |
| 2018/0021354 A1 | 1/2018 | Petkovich et al. |

FOREIGN PATENT DOCUMENTS

| | | |
|---|---|---|
| DE | 20321698 U1 | 12/2008 |
| EP | 0 227 836 A1 | 7/1987 |
| EP | 0413828 A1 | 2/1991 |
| EP | 0 508 756 A1 | 10/1992 |
| EP | 0387808 B1 | 5/1993 |
| EP | 0629405 A1 | 12/1994 |
| EP | 1080055 A2 | 3/2001 |
| EP | 1208843 A1 | 5/2002 |
| EP | 1165061 B1 | 10/2005 |
| EP | 1980255 A1 | 10/2008 |
| EP | 2148661 B1 | 12/2012 |
| EP | 2591354 A1 | 5/2013 |
| EP | 2037936 B1 | 6/2014 |
| JP | 55-139320 | 10/1980 |
| JP | 57-188520 A | 11/1982 |
| JP | 58-032823 | 2/1983 |
| JP | 58-206524 A | 12/1983 |
| JP | 64-031722 A | 2/1989 |
| JP | 02-229115 A | 9/1990 |
| JP | 04-198129 A | 7/1992 |
| JP | 04-208225 A | 7/1992 |
| JP | H04288016 A | 10/1992 |
| JP | 07-242550 A | 9/1995 |
| JP | 08-092098 A | 4/1996 |
| JP | 10-158171 A | 6/1998 |
| JP | 11-158074 A | 6/1999 |
| JP | 2001-512418 A | 8/2001 |
| JP | 2002-302447 A | 10/2002 |
| JP | 2004-175750 A | 6/2004 |
| JP | 2004-531548 A | 10/2004 |
| JP | 2005-505589 A | 2/2005 |
| JP | 2005-513419 A | 5/2005 |
| JP | 2005-528383 A | 9/2005 |
| JP | 2005-531532 A | 10/2005 |
| JP | 2005-535682 A | 11/2005 |
| JP | 2005-538189 A | 12/2005 |
| JP | 2006-517593 A | 7/2006 |
| JP | 2006-523221 A | 10/2006 |
| JP | 2007-525472 A | 9/2007 |
| JP | 2010-506520 A | 2/2010 |
| JP | 2010-525079 A | 7/2010 |
| JP | 2011-512343 A | 4/2011 |
| JP | 2012-515738 A | 7/2012 |
| KR | 10-2012-0005228 A | 1/2012 |
| WO | WO-91/12807 A1 | 9/1991 |
| WO | WO-91/16899 A1 | 11/1991 |
| WO | 92/09271 A1 | 6/1992 |
| WO | WO-94/00128 A1 | 1/1994 |
| WO | 96/01621 A1 | 1/1996 |
| WO | WO-96/00074 A1 | 1/1996 |
| WO | WO-96/31215 A1 | 10/1996 |
| WO | WO-97/11053 A1 | 3/1997 |
| WO | WO-98/18610 A1 | 5/1998 |
| WO | 98/29105 A2 | 7/1998 |
| WO | WO-99/11272 A1 | 3/1999 |
| WO | 99/49027 A1 | 9/1999 |
| WO | 99/61398 A2 | 12/1999 |
| WO | WO-00/21504 A1 | 4/2000 |
| WO | WO-00/35419 A2 | 6/2000 |
| WO | 00/60109 A1 | 10/2000 |
| WO | 00/61123 A2 | 10/2000 |
| WO | 01/37808 A1 | 5/2001 |
| WO | WO 01/72286 * | 10/2001 |
| WO | 02/92056 A1 | 11/2002 |
| WO | 03/09572 A1 | 1/2003 |
| WO | 03/30869 A1 | 4/2003 |
| WO | WO-03/039521 A1 | 5/2003 |
| WO | WO-03/039572 A1 | 5/2003 |
| WO | 03/45381 | 6/2003 |
| WO | WO-03/047595 A1 | 6/2003 |
| WO | 03/86267 A2 | 10/2003 |
| WO | 03/86415 A1 | 10/2003 |
| WO | 03/88976 A1 | 10/2003 |
| WO | 03/93459 | 11/2003 |
| WO | 2003/106411 A1 | 12/2003 |
| WO | 2004/010981 A1 | 2/2004 |
| WO | WO-2004/028515 A1 | 4/2004 |
| WO | 2004/054968 A2 | 7/2004 |
| WO | WO-2004/058235 A2 | 7/2004 |
| WO | WO-2004/080467 A2 | 9/2004 |
| WO | 2004/110381 A2 | 12/2004 |
| WO | 2004/110391 A2 | 12/2004 |
| WO | 2005/000268 A2 | 1/2005 |
| WO | 2005/003358 A1 | 1/2005 |
| WO | WO-2005/011652 A2 | 2/2005 |
| WO | WO-2005/123120 A1 | 12/2005 |
| WO | 2006/052452 A1 | 5/2006 |
| WO | 2006/059180 A2 | 6/2006 |
| WO | 2006/113505 A2 | 10/2006 |
| WO | WO2007092755 * | 2/2007 |
| WO | 2007/039193 A1 | 4/2007 |
| WO | 2007/039569 A2 | 4/2007 |
| WO | WO-2007/047327 A2 | 4/2007 |
| WO | 2007/050724 A2 | 5/2007 |
| WO | 2007/050975 A2 | 5/2007 |
| WO | 2007/053608 A2 | 5/2007 |
| WO | 2007/068287 A1 | 6/2007 |
| WO | 2007/092221 A2 | 8/2007 |
| WO | WO-2007/092755 A2 | 8/2007 |
| WO | 2007/146004 A1 | 12/2007 |
| WO | WO-2008/008608 A2 | 1/2008 |
| WO | 2008/043449 A1 | 4/2008 |
| WO | WO-2008/097646 A1 | 8/2008 |
| WO | 2008/116113 A1 | 9/2008 |
| WO | 2008/116133 A1 | 9/2008 |
| WO | 2008/134518 A2 | 11/2008 |
| WO | WO-2008/134512 A1 | 11/2008 |
| WO | WO-2008/134523 A1 | 11/2008 |
| WO | 2009/047644 A2 | 4/2009 |
| WO | 2009/101132 A1 | 8/2009 |
| WO | 2009/101135 A1 | 8/2009 |
| WO | 2009/101137 A1 | 8/2009 |
| WO | 2009/124210 A1 | 10/2009 |
| WO | WO-2010/011906 A1 | 1/2010 |
| WO | 2010/034342 A1 | 4/2010 |
| WO | 2011/031621 A2 | 3/2011 |
| WO | 2011/063952 A1 | 6/2011 |
| WO | 2011/095388 A1 | 8/2011 |
| WO | 2011/123476 A1 | 10/2011 |

(56) References Cited

FOREIGN PATENT DOCUMENTS

| | | | |
|---|---|---|---|
| WO | 2012/006475 A1 | 1/2012 | |
| WO | 2012/018329 A1 | 2/2012 | |
| WO | 2012/076429 A1 | 6/2012 | |
| WO | 2012/091569 A1 | 7/2012 | |
| WO | 2012/117236 A1 | 9/2012 | |
| WO | 2012/145491 A2 | 10/2012 | |
| WO | 2014/029953 A1 | 2/2014 | |
| WO | 2014/143941 A1 | 9/2014 | |
| WO | 2014/193255 A1 | 12/2014 | |
| WO | 2014/202754 A1 | 12/2014 | |
| WO | 2016/020508 A2 | 2/2016 | |

OTHER PUBLICATIONS

Barreto et al. (Cancer Epidmiol Biomarkers Prev 2000; 265-270, published online Mar. 1, 2000.*
Haddad et al. (JCE & M, 1976, vol. 43, No. 1, pp. 86-91).*
Blunt et al., (Blunt et al. (Proc. N. A. S. Biochemistry, pp. 1503-1506, Aug. 5, 1968, 892 ref.).*
Heike A. A. Bischoff-Ferrari (J. of Steroid & Molecular Biology 103 (2007) 614-619).*
Haddad et al. (J Clin Endocrinol Metab 42: 284, 1976).*
B.P. Halloran (J. of Clinical Endocrinology and Metabolism (vol. 59, No. 8, pp. 1063-1069).*
Barger-Lux et al. (Osteoporosis Int. (1998), 8:222-230).*
Goldzieher JW(Endocr Pract. Sep.-Oct. 1999;5(5):229-32).*
"ACP Formulary and Pocket Guide to Psychopharmacology," Virginia DMHMRSAS, vol. 1, Iss. 1 (2004-2005).
Boxtel et al., "Drug Benefits and Risks, International Textbook of Clinical Pharmacology," p. 75-76 (2001).
Centorrino et al., "Multiple versus single antipsychotic agents for hospitalized psychiatric patients: case-control study of risks versus benefits," Am J. Psychiatry, 161 (4): 700-06 (2004).
Fournier et al., "Traitement vitaminique D et osteodystrophies renales: indications et modalities," Nephrologie 16(2): 165-90 (1995).
Holick et al., "Vitamin D2 is as effective as vitamin D3 in maintaining circulating concentrations of 25-hydroxyvitamin D," J Clin Endocrinol Metab., 93(3):677-81 (2008).
"Guidance for Industry, Nonclinical Safety Evaluation of Drug or Biologic Combinations," U.S. Department of Health and Human Services, Food and Drug Administration (Mar. 2006).
Martin, E.W., "Drug Interactions," in Hazards of Medication, J.B. Lippincott Co. (1978).
"K/DOQI Clinical Practice Guidelines for Bone Metabolism and Disease in Chronic Kidney Disease," National Kidney Foundation, Am. J. Kidney Dis., 42 (Supplement 3):1-202 (2003).
Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).
Andress, "Vitamin D in chronic kidney disease: A systematic role for selective vitamin D receptor activation," Kidney Int., 69:33-43 (2006).
Arekat et al., "Dramatic Improvement of BMD Following Vitamin D Therapy in a Bone Marrow Transplant Recipient," J. Clin. Densitometry, 5:267-271 (2002).
Armas et al., "Vitamin $D_2$ is Much Less Effective than Vitamin $D_3$ in Humans," J. Clin. Endocrinol. Metab., 89:5387-5391 (2004).
Bagnis et al., "Biochemical and Hormonal Short-Term Effects of 25-hydroxyvitamin D3 in Patients on Continuous Peritoneal Dialysis," Ital. J. Mineral Electrolyte Metab., 12:73-76 (1998).
Bailie et al. "Comparative Review of the Pharmacokinetics of Vitamin D Analogues," Seminars in Dialysis, 15(5):352-357 (2000).
Baird et al., "Steroid Dynamics Under Steady-State Conditions," Recent Prog. Horm. Res., 25:611-664 (1969).
Barger-Lux M.J et al., "Vitamin D And Its Major Metabolites: Serum Levels After Graded Oral Dosing In Healthy Men" Osteoporosis International, United Kingdom, 8(3):222-230 (1998).

Barreto et al., "25-Hydroxyvitamin $D_3$, the Prohormone of 1,25-Dihydroxyvitamin $D_3$, Inhibits the Proliferation of Primary Prostatic Epithelial Cells," Cancer Epidemiol, Biomarkers & Prevention, 9:265-270 (2000).
Beckman, et al., "Up-Regulation of the Intestinal 1,25-Dihydroxyvitamin D Receptor During Hypervitaminosis D: A Comparison Between Vitamin D2 and Vitamin D31," Biochemical and Biophysical Research Communications, vol. 169, No. 3, pp. 910-915 (Jun. 29, 1990).
Beer et al., "Pharmacokinetics and Tolerability of a Single Dose of DN-101, a New Formulation of Calcitriol, in Patients with Cancer," Clin. Cancer Res., 11:7794-7799 (2005).
Bell et al., "Evidence that 1,25-Dihydroxyvitamin D3 Inhibits the Hepatic Production of 25-Hydroxyvitamin D in Man," J. Clin. Invest., 74:1540-1544 (1984).
Belostotsky et al., "A single high dose of ergocalciferol can be used to boost 25-hydroxyvitamin D levels in children with kidney disease," Pediatr Nephrol, 24:625-626 (2009).
Bianchi et al., "No Difference in Intestinal Strontium Absorption After an Oral or an Intravenous 1,25(OH)$_2$D$_3$ Bolus in Normal Subjects," J. Bone Miner. Res., 14:1789-1795 (1999).
Blair et al., "Prevalence of vitamin D [25(OH)D] deficiency and effects of supplementation with ergocalciferol (vitamin D2) in stage 5 chronic kidney disease patients." J.Ren Nutr., 18: 375-382 (2008).
Bordier et al., "Evolution of renal osteodystrophy: Correlation of bone histomorphometry and serum mineral and immunoreactive parathyroid hormone values before and after treatment with calcium carbonate or 25-hydroxycholecalciferol," Kidney Int Suppl, 2:S102-S112 (1975).
Bouillon et al., "Influence of dialysate calcium concentration and vitamin D on serum parathyroid hormone during repetitive dialysis," Kidney Int., 7:422-432 (1975).
Brassard et al. "Influence of Glomerular Filtration Rate on Non-(1-84) Parathyroid Hormone (PTH) Detected by Intact PTH Assays," Clinical Chemistry, 46(5):697-703 (2000).
Buccianti et al., "Effects of Calcifediol Treatment on the Progression of Renal Osteodystrophy during Continuous Ambulatory Peritoneal Dialysis," Nephron, 56:353-356 (1990).
Budavari (ed.), Merck Index: an Encyclopedia of Chemicals, Drugs, and Biologicals, 11th Edition, Merck & Co., 9927-9930 (1989).
Bulla et al., "Renal bone disorders in children: therapy with vitamin D3 or 1,25-dihydroxycholecalciferol," Proc.Eur.Dial.Transplant. Assoc., 16: 644-648 (1979).
Chandra et al., "Cholecalciferol (vitamin D3) therapy and vitamin D insufficiency in patients with chronic kidney disease: a randomized controlled pilot study," Endocr.Pract., 14: 10-17 (2008).
Claris-Appiani et al., "Phosphate-Induced PTH Stimulation and Calcitriol Treatment in Children with Early Chronic Renal Insufficiency," J. Bone Miner. Met., 12:S91-S97 (1994).
Coburn, "An Update on Vitamin D as Related to Nephrology Practice: 2003," Kidney International, vol. 64, Supplement 87, pp. S125-S130 (2003).
Coburn, et al., "Use of Active Vitamin D Sterols in Patients with Chronic Kidney Disease, Stages 3 and 5," Kidney International, vol. 63, Supplement 85, pp. S49-S53 (2003).
Coen et al., "1,25(OH)$_2$D$_3$ and 25-OHD$_3$ in the Treatment of Renal Osteodystrophy: Comparison of Combined Versus 1,25(OH)$_2$D$_3$ Administration Alone," Miner. Electrolyte Metab., 9:19-27 (1983).
Coen et al., "25-hydroxycholecalciferol in the treatment of renal osteodystrophy in haemodialysed patients," Int J Artificial Organs, 2(6): 278-281 (1979).
Cohen-Solal et al., "Non-Aluminic Adynamic Bone Disease in Non-Dialyzed Uremic Patients: A New Type of Osteopathy Due to Overtreatment?" Bone, 13:1-5 (1992).
Collet et al. "Modified-Release Peroral Dosage Forms," Aulton (ed.), Pharmaceutics: The Science of Dosage Forms, Churchill Livingston, London, pp. 289-305 (2002).
Colodro et al., "Effect of 25-Hydroxy-Vitamin D3 on Intestinal Absorption of Calcium in Normal Man and Patients With Renal Failure," Metabolism, 27(6):745-753 (1978).
Cooke et al., "Vitamin D-Binding Protein (Gc-Globulin): Update 1995," Endocrine Rev., 4:125-128 (1995).

(56) References Cited

OTHER PUBLICATIONS

Coyne et al., "Paricalcitol Capsule for the Treatment of Secondary Hyperparathyroidism in Stages 3 and 4 CKD," *American Journal of Kidney Diseases*, 47(2):263-276 (2006).
Daisley-Kydd et al., "Calcitriol in the Management of Secondary Hyperparathyroidism of Renal Failure," *Pharmacotherapy.*, 16:619-630 (1996).
Davies, M. et al. The Absorption and Metabolism of Vitamin D3 from Parenteral Injection Sites', Proceedings of the Workshop on Vitamin D, 4th, Vitam. D: Basic Res. Its Clin. Appl. (1979), abstract.
DB-Pharma, "Dedrogyl 15 Mg/10ML Calcifediol Oral Drops, Solution," Marketing Authorization No. 317 863.2 (2000).
DeLuca, "Treatment of renal osteodystrophy with 25-hydroxycholecalciferol," *Arch Intern Med*, 126(5):896-899 (1970).
Deroisy et al., "Comparison of the Short-Term Effects of Three Oral Calcium-Vitamin D Formulations and Placebo on Calcium Metabolism," *Curr. Ther. Res.*, 59:370-378 (1998).
DeVille et al., "Effect of Ergocalciferol Supplementation on Serum Parathyroid Hormone and Serum 25-Hydroxyvitamin D in Chronic Kidney Disease," *Nephrology*, 11:555-559 (2006).
*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).
*Dietary Supplement Fact Sheet: Vitamin D*, National Institutes of Health, Office of Dietary Supplements (last update: Aug. 5, 2005), retrieved from <URL:http:ods.od.nih.gov/factsheets/vitamind.asp>on Aug. 31, 2007.
*Disease and Vitamin D*, University of California Riverside, retrieved from Internet, <URL: <http://vitamind.ucr.edu/disease.html>> (last update: May 19, 1999).
Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.
Dogan et al., "Effect of depot oral cholecalciferol treatment on secondary hyperparathyroidism in stage 3 and stage 4 chronic kidney diseases patients," *Ren Fail.*, 30: 407-410 (2008).
Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).
Dusso et al, "Metabolic Clearance Rate and Production Rate of Calcitriol in Uremia," *Kidney Int.*, 35 860-864 (1989).
Dusso et al., "Extra-renal production of calcitriol in chronic renal failure," *Kidney Int.*, 34:368-375 (1988).
Dusso et al., "Extrarenal Production of Calcitrol in Normal and Uremic Humans*," *Journal of Clinical Endocrinology and Metabolism*, 72(1):157-164 (1991).
Eastwood et al., "Biochemical and histological effects of 1,25 dihydroxycholecalciferol (1,25-DHCC) in the osteomalacia of chronic renal failure," *J Urol Nephrol (Paris,)* 80(12): 984-985 (1974).
Eastwood et al., "The contrasting effects on bone histology of vitamin D and of calcium carbonate in the osteomalacia of chronic renal failure," *Clin Sci Molec Med*, 47:23-42 (1974).
Eastwood et al., "The Effect of 25-Hydroxy Vitamin $D_3$ in the Osteomalacia of Chronic Renal Failure," *Clin. Sci. Molec. Med.*, 52:499-508 (1977).
Fernandez et al., "Guidelines for Dosing of Intravenous Calcitriol in Dialysis Patients with Hyperparathyroidism," *Nephrol. Dial. Transplant.*, 11:96-101 (1996).
Fournier et al., "1-alpha-Hydroxycholecalciferol and 25-Hydroxycholecalciferol in Renal Bone Disease," *Calcified Tissues 1975: Proceedings of the 11th European Symposium on Calcified Tissues*, 226-235 (1975).
Fournier et al., "1α Hydroxycholecalciferol and 25 Hydroxycholecalciferol in Renal Bone Disease" Proc Eur Dial Transplant Assoc 12:227-236 (1976).

Fournier et al., "Advances in Nephrology from the Necker Hospital" *Adv. Nephrol Necker Hosp.* 21:237-306 (1992).
Fournier et al., "Comparison of 1α-hydroxycholecalciferol and 25-hydroxycholecalciferol in the treatment of renal osteodystrophy: Greater effect of 25-hydroxycholecalciferol on bone mineralization" Kidney International 15:196-204 (1979).
Fournier et al., "Current Status of the Management of Renal Osteodystrophy" *Proceedings of the European Dialysis and Transplant Association* 15:547-568 (1978).
Fournier et al., "Importance of Vitamin D Repletion in Uraemia," *Nephrol Dial Transplant*, 14(4):819-823 (1999).
Fournier et al., "Low doses of calcitriol or calcium carbonate for the prevention of hyperparathyroidism in predialysis patients?" *Nephrol Dial Transplant* 11(7):1493-1495 (1996).
Fournier et al., "Present-Day Concepts in the Treatment of Chronic Renal Failure" *Contrib Nephrol.* 71:64-80 (1989).
Fournier et al., "Preventing Renal Bone Disease in Moderate Renal Failure with $CaCO_3$ and 25(OH) Vitamin $D_3$," *Kidney Int.*, 33:S178-S279 (1988).
Fournier et al., "Renal Osteodystrophy in Dialysis Patients: Diagnosis and Treatment," *Artificial Organs*, 22:530-557 (1998).
Fournier et al., "Renal Osteodystrophy: Pathophysiology and Treatment" *Hormone Res.* 20:44-58(1984).
Fournier et al., "The Approach to the Treatment of Secondary Hyperparathyroidism in Early Renal Failure" *Am. J. Nephrol* 8:170-172 (1988).
Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).
Friedman et al. "The Role of Vitamin D in Mild to Moderate Chronic Kidney Disease," *Trends in Endocrinology & Metab,.* 13(5):189-194 (2002).
Frohling et al., "Serum 25-hydroxyvitamin D in patients with chronic renal failure on long-term treatment with high doses of vitamin D2." *Nephron* 26: 116-120 (1980).
Frost et al., "Histomorphometric Changes in Trabecular Bone of Renal Failure Patients Treated with Calcifediol," *Metab. Bone Dis. & Rel. Res.*, 2:285-295 (1981).
Gallagher et al., "Comparison of the Histological Effect and Metabolism of 25-(OH)D and 1,25-(OH)2D in Rat Bone," p. 399-401, In: *Norman, Vitamin D: Basic Research and its Clinical Application: Proceedings of the Fourth Workshop on Vitamin D, Berlin, West Germany, Feb. 1979.*
Ghazali et al., "Is low plasma 25-(OH) vitamin D a major risk factor for hyperparathyroidism and Looser's zones independent of calcitriol?" *Kidney International* 55:2169-2177 (1999).
Haddad et al., "Acute Administration of 25-Hydroxycholecalciferol in Man," *J. Clin. Endocrinol. Metab.*, 42:284-289 (1976).
Haddad et al., "Human Serum Binding Capacity and Affinity for 25-Hydroxyergocalciferol and 25-Hydroxycholecalciferol," *J. Clin. Endocrinol. Metab.*, 43:86-91 (1976).
Haddad et al., "Natural and Synthetic Sources of Circulating 25-Hydroxyvitamin D in Man," *Nature*, 244:515-517 (1973).
Haddad, "Plasma Vitamin D-binding Protein (Gc-Globulin): Multiple Tasks," *J. Steroid Biochem. Molec. Biol.*, 53:579-582 (1995).
Haddad, "Seasonal Diminution of Vitamin D Stores in the United States: Can Darker Winters Lead to Lighter Bones?" *Trends Endocrinol. Metab.*, 7:209-212 (1996).
Haddad, "Traffic, Binding and Cellular Access of Vitamin D Sterols," *Bone and Mineral Res.*, Elsevier, 5:281-308 (1987).
Haddad, "Vitamin D—Solar Rays, The Milky Way, or Both?" *NEJM*, 326:1213-1215 (1992).
Haldimann et al., "Effect of an Oral Dose of 25-Hydroxyvitamin D3 on Its Blood Levels in Patients with the Nephrotic Syndrome," *J Clin Endocrinology and Metabolism*, 50(3): 470-474 (1980).
Halloran et al., "Plasma Vitamin D Metabolite Concentrations in Chronic Renal Failure: Effect of Oral Administration of 25-Hydroxyvitamin D3," *J. Clin. Endocrin. & Metab.*, 59:1063-1069 (1984).
Hamida et al., "Hyperparathyroïdie secondaire álinsuffisance rénale" Annales d'Endocrin-ologie 55:147-158 (1994) [reference in French].

(56) References Cited

OTHER PUBLICATIONS

Hannula et al., "Constant, But Not Pulsed Calcitriol Suppresses Hemodialysis Patients' Antigen-Induced Lymphocyte Proliferation," *Nephron,* 86:139-144 (2000).
Hari et al., "Vitamin D insufficiency and effect of cholecalciferol in children with chronic kidney disease," *Pediatr.Nephrol,*. 25: 2483-2488 (2010).
Hay et al., "Vitamin D2 in Vertebrate Evolution," *Comp. Biochem. Physiol. B,* 56:375-380 (1977).
Hodson et al., "Treatment of childhood renal osteodystrophy with calcitriol or ergocalciferol," *Clin Nephrology,* 24(4): 192-200 (1985).
Holick, "Vitamin D Deficiency in CKD: Why Should We Care?" *Am. J. Kidney Dis.,* 45:1119-1121 (2005).
Holick, "Vitamin D Status: Measurement, Interpretation and Clinical Application," *Ann Epidemiol,* 19(2):73-78 (2009).
Hollis, "Circulating 25-Hydroxyvitamin D Levels Indicative of Vitamin D Sufficiency: Implications for Establishing a New Effective Dietary Intake Recommendation for Vitamin D," *J. Nutr.* 135: 317-322 (2005).
Horst et al., "A Sensitive Competitive Protein Binding Assay for Vitamin D in Plasma," *Steroids,* 37:581-592 (1981).
Horst et al., "Discrimination in the Metabolism of Orally Dosed Ergocalciferol and Cholecalciferol by the Pig, Rat and Chick," *Biochem. J.,* 204:185-189 (1982).
Horst et al., "Rat cytochrome P450C24 (CYP24) does not metabolize 1,25-dihydroxyvitamin $D_2$ to calcitroic acid," *J. Cell Biochem.,* 88:282-285 (2003).
Hottelart et al., "Ostéodystrophie rénale (2): son traitement chez l'insuffisant rénal avant la dialyse" *Nephrologie* 21 (6):275-282 (2000) [reference in French].
Houghton et al., "The Case Against Ergocalciferol (Vitamin $D_2$) as a Vitamin Supplement," *Am. J. Clin. Nutr.,* 84:694-697 (2006).
Hunt, et al., "A Comparison of the Toxicity of Ergocalciferol and Cholecalciferol in Rhesus Monkeys (*Macaca mulatta*)," J. Nutrition, 102:975-986 (1972).
Hussar, "New Drugs of 1999," *J. Am. Pharmacist. Assoc.* 40(2):181-229 (2000).
International Search Report for Application No. PCT/IB2008/003480, dated Mar. 31, 2009.
International Search Report for Application No. PCT/US2007/061521, dated Jul. 17, 2007.
International Search Report for Application No. PCT/US2008/061579, dated Aug. 21, 2008.
Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," *Kidney Int.,* 55:1019-1027 (1999).
Jara et al., "Effect of Calcitriol Treatment and Withdrawal on Hyperparathyroidism in Haemodialysis Patients with Hypocalcaemia," *Nephrol. Dial. Transplant,* 16:1009-1016 (2001).
Jean et al., "Daily Oral 25-Hydroxycholecalciferol Supplementation for Vitamin D Deficiency in Haemodialysis Patients: Effects on Mineral Metabolism and Bone Markers," *Nephrol. Dial. Transplant,* 23:3670-3676 (2008).
Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" *Nephron. Clin. Pract.* 110:c58-c65 (2008).
Jean et al., "Monthly cholecalciferol administration in heamodialysis patients: a simple and efficient strategy for vitamin D supplementation" *Nephrol. Dial. Transplant* 24(12):3799-3805 (2009).
Jones, "Pharmacokinetics of vitamin D toxicity," *Am. J. Clin. Nutr.* 88(suppl): 582S-6S (2008).
Jones., "Expanding the Role for Vitamin D in Chronic Kidney Disease: Importance of Blood 25-OH-D Levels and Extra-Renal 1α-Hydroxylase in the Classical and Nonclassical Actions of 1α, 25-Dihydroxyvitamin $D_3$," *Seminars in Dialysis,* 20(4):316-324 (2007).
Kajihara et al., "Novel Method to Control Release of Lipophilic Drugs with High Potency from Silicone," *Chem. Pharm. Bull.,* 51:11-14 (2003).
Kalantar-Zadeh et al., "Clinical Outcomes with Active versus Nutritional Vitamin D Compounds in Chronic Kidney Disease" *Clin J Am Soc Nephrol.* 4(9):1529-1539 (2009).
Kanis et al., "Rate of Reversal of Hypercalcaemia and Hypercalciuria Induced by Vitamin D and Its 1-alpha-Hydroxylated Derivatives," *BMJ,* 1:78-81 (1977).
Kim, *Advanced Pharmaceutics: Physicochemical Principles,* pp. 362-392, Boca Raton, Fla: CRC Press (2004).
Kleinman et al., "Effects of Calcifediol on Calcified Tissue in Uremia," *Arch Intern Med,* 138: 864-865 (1978).
Kooienga et al., "The effect of combined calcium and vitamin D3 supplementation on serum intact parathyroid hormone in moderate CKD," *Am.J.Kidney Dis,*. 53: 408-416 (2009).
Koshikawa, et al., "Clinical Effect of Intravenous Calcitriol Administration on Secondary Hyperparathyroidism," *Nephron;* 90:413-423 (2002).
LaClair et al., "Prevalence of Calcidiol Deficiency in CKD: A Cross-Sectional Study Across Latitudes in the United States," *Am. J. Kidney Dis.,* 45:1026-1033 (2005).
Lafage et al., "Ketodiet, Physiological Calcium Intake and Native Vitamin D Improve Renal Osteodystrophy," *Kidney Int.,* 42:1217-1225 (1992).
Lambert et al., "Evidence for Extranrenal Production of 1-alpha,25-Dihydroxyvitamin D in Man," *J. Clin. Invest.,* 69:722-725 (1982).
Lambrey et al., "24, 25 Dihydroxycalciferol: Assay in Non-Anephric Patients on Chronic Haemodialysis and Assessment of it's Possible Pathophysiological Role in Renal Osteodystrophy" *Proc Eur Dial Transplant Assoc.* 17:548-556 (1980).
Lambrey, "Possible Link Between Changes in Plasma 24,25-Dihydroxyvitamin D and Healing of Bone Resorption in Dialysis Osteodrstrophy" *Metab. Bone Dis. & Rel. Res.* 4:25-30 (1982).
Langman et al., "25-Hydroxyvitamin D3 (Calcifediol) Therapy of Juvenile Renal Osteodystrophy: Beneficial Effect on Linear Growth Velocity," *J. Pediatrics,* 100:815-820 (1982).
Larrosa M. et al., Long-Term Treatment of Hypovitaminosis D. Calcidol Or Cholecalciferol? *Annals Of The Rheumatic Diseases,* vol. 64, No. Suppl. 3, Jul. 2005, p. 366.
Lau et al., "Vitamin D Therapy of Osteoporosis: Plain Vitamin D Therapy Versus Active Vitamin D Analog (D-Hormone) Therapy," *Calcif. Tissue Int.,* 65:295-306 (1999).
Lehmann et al., "Coating of Tablets and Small Particles with Acrylic Resins by Fluid Bed Technology," *Int. J. Pharm. Tech. & Prod. Mfr.,* 2:31-43 (1981).
Letteri et al., "Effects of 25-Hydroxycholecalciferol on Calcium Metabolism in Chronic Renal Failure" Adv. Exp. Med. Biol. 81:591-601 (1977).
Lips et al., "A Global Study of Vitamin D Status and Parathyroid Function in Postmenopausal Women with Osteoporosis: Baseline Data from the Multiple Outcomes of Raloxifene Evaluation Clinical Trial," *The Jour. of Clin. Endo. & Meta.,* 86(3):1212-1221 (2001).
Lomonte et al., "Are Low Plasma Levels of 25-(OH) Vitamin D a Major Risk Factor for Hyperparathyroidism Independent of Calcitriol in Renal Transplant Patients?" *J. Nephrol.,* 18:96-101 (2005).
Lund et al., "Serum 1,25-Dihydroxycholecalciferol in Anephric. Haemodialyzed and Kidney-transplanted Patients," *Nephron,* 25:30-33 (1980).
Maierhofer et al., "Synthesis and Metabolic Clearance of 1,25-Dihydroxyvitamin D as Determinants of Serum Concentrations: a Comparison of Two Methods" Journal of Clinical Endocrinology and Metabolism 53:472-475 (1981).
Manni et al., "Oral Calcitriol: Comparison Between the Same Weekly Dose Administered as a Single vs. Two Divided Pulsed Doses in Secondary Hyperparathyroidism of Chronic Renal Failure," *Ital. J Mineral Electrolyte Metab.,* 11:61-64 (1997).
Matsushita et al., "Clinical effects of 25-hydroxycholecalciferol in patients with chronic renal failure," *J Nutr Sci Vitaminol,* 23:257-261 (1977).
Mazouz et al., "Risk factors of renal failure progression two years prior to dialysisis" Clinical Nephroloby 51 (6):355-366 (1999).

(56) References Cited

OTHER PUBLICATIONS

Mazur, "Effects of 25-OHD3 on Renal Function in Pediatric Patients with Chronic Renal Failure," *Mineral Electrolyte Metab.* 10:351-358 (1984).
Memmos et al., "Response of uremic osteoid to vitamin D," *Kidney Int*, 21 (Suppl. 11): S50-S54 (1982).
Menon et al., "Vitamin D insufficiency and hyperparathyroidism in children with chronic kidney disease," Pedaitr Nephrol, 23:1831-1836 (2008).
Messa et al., "Direct In Vivo Assessment of Parathyroid Hormone-Calcium Relationship Curve in Renal Patients," *Kidney Int.*, 46:1713-1720 (1994).
Moe et al., "A randomized trial of cholecalciferol versus doxercalciferol for lowering parathyroid hormone in chronic kidney disease," *Clin.J.Am.Soc.Nephrol.* 5: 299-306 (2010).
Moe et al., "Safety and Efficacy of Pulse and Daily Calcitriol in Patients on CAPD: A Randomized Trial," *Nephrol. Dial. Transplant.*, 13:1234-1241 (1998).
Morris, "Vitamin D: A Hormone for All Seasons—How Much is Enough?" *Clin. Biochem. Rev.*, 26:21-32 (2005).
Muindi et al., "Phamacokinetics of Liquid Calcitriol Formulation in Advanced Solid Tumor Patients: Comparison with Caplet Formulation," *Cancer Chemother. Pharmacol.*, 56:492-496 (2005).
Naik et al., "Effects of Vitamin D Metabolites and Analogues on Renal Function," *Nephron*, 28:17-25 (1981).
Nakanishi et al., "The Roles of Vitamin D in Secondary Hyperparathyroidism," [journal in Japanese] 52:1107-1112 (2004).
Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Oksa et al., "Effects of long-term cholecalciferol supplementation on mineral metabolism and calciotropic hormones in chronic kidney disease," *Kidney Blood Press Res.*, 31: 322-329 (2008).
Parfitt et al., "Calcitriol But No Other Metabolite of Vitamin D is Essential for NormalBone Growth and Development in the Rat," *J. Clin. Invest.*, 73:576-586 (1984).
Peacock et al., "Effect of Calcium or 25OH Vitamin D3 Dietary Supplementation on Bone Loss at the Hip in Men and Women over the Age of 60" *The Journal of Clinical Endocrinology & Metabolism*, 85(9):3011-3019 (2007).
Phadnis et al., "Direct, Rapid Effects of 25-Hydroxyvitamin D3 on Isolated Intestinal Cells," *J. Cell. Biochem.*, 90:287-293 (2003).
Pourgholami et al., "1, 25-Dihydroxyvitamin $D_3$ Dissolved in Lipiodol Produces a Sustained Antiproliferative Effect in the Human Hepatoblastoma Cell Line HepG2," *Anticancer Res.*, 20:723-728 (2000).
Pourgholami et al., "In Vitro Antiproliferative Activity of a Medium-Chain Triglyceride Solution of 1, 25-Dihydroxyvitamin $D_3$ in HepG2 Cells," *Anticancer Res.*, 20:4257-4260 (2000).
Rapuri, P.B. et al., "Effect of Vitamins D2 and D3 Supplement Use on Serum 25-OHD Concentration in Elderly Women in Summer and Winter," Calcified Tissue International, 74(2):150-156 (2004).
Recker et al., "The Efficacy of Calcifediol in Renal Osteodystrophy," *Arch. Intern. Med.*, 138:857-863 (1978).
Reddy et al., Abstracts Sixth Annual Scientific Meeting of the American Society for Bone and Mineral Research, 36:524 (1984).
Reichel et al., "Calcium Metabolism in Early Chronic Renal Failure: Implications for the Pathogenesis of Hyperparathyroidism," *Nephrol. Dial. Transplant.*, 6:162-169 (1991).
Reichel et al., "Intermittent Versus Continuous Administration of 1,25-dihydroxyvitamin $D_3$ in experimental renal hyperparathyroidism," *Kidney Int.*, 44:1259-1265 (1993).
Reichel, "Current treatment options in secondary renal hyperparathyroidism," *Nephrol Dial Transplant* 21:23-28 (2006).
Ritter et al., "25-Hydroxyvitamin $D_3$ suppresses PTH synthesis and secretion by bovine parathyroid cells," *Kidney Int.*, 70:654-659 (2006).

Rucker et al., "Vitamin D insufficiency and treatment with oral vitamin D3 in northern-dwelling patients with chronic kidney disease," *J.Nephrol.* 22: 75-82 (2009).
Russell et al., "Therapeutic Effects of 25-Hydroxyvitamin D3 on Renal Osteodystrophy," *Mineral Electrolyte Metab.*, 1:129-138 (1978).
Rutherford et al., "Effect of 25-Hydroxycholecalciferol on Calcium Absorption in Chronic Renal Disease," Kidney International, 8:320-324 (1975).
Saab et al., "Prevalence of Vitamin D Deficiency and the Safety and Effectiveness of Monthly Ergocalciferol in Hemodialysis Patients," *Nephron Clin. Pract.*, 105:c132-c138 (2007).
Sanchez, "Prevention and Treatment of Renal Osteodystrophy in Children With Chronic Renal Insufficiency and End-Stage Renal Disease," *Seminars in Nephrology*, 21:441-450 (2001).
Sebert et al., "Effets A Long Terme D'Une Association De 25-Hydroxycholécalciférol et de 1-Alpha-Hydroxycholécalciférol Sur L'Ostéodystrophie Des Hémodialysés Chroniques" Rev. Rhum Mal Osteoartic 48(7-9):535-541 (1981).
Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," *Metab. Bone Dis. & Rel. Res.*, 2:217-222 (1980).
Sekkarie, "The Impact of Over-the-counter Vitamin D Supplementals on Vitamin D and Parathyroid Hormone Levels in Chronic Kidney Disease," *Clin. Nephrology*, 65:91-96 (2006).
Shah et al., "Prevalence and correction of 25(OH) vitamin D deficiency in peritoneal dialysis patients," *Peritoneal Dialysis Int.*, 25:362-366 ( 2005).
Sjoden, et al., "1α-Hydroxyvitamin $D_2$ is Less Toxic than 1α-Hydroxyvitamin $D_3$ in the Rat," Society for Experimental Biology and Medicine, 179: 432-436 (1985).
Somerville et al., "Resistance to Parathyroid Hormone in Renal Failure: Role of Vitamin D Metabolites," *Kidney Int.*, 14:245-254 (1978).
Sommerfeldt et al., "Metabolism of Orally Administered [$^3$H]Ergocalciferol and [$^3$H]Cholecalciferol by Dairy Calves," *J. Nutr.*, 113:2595-2600 (1983).
Soob et al., "Prevalence of Vitamin D Deficiency and the Safety and Effectiveness of Monthly Ergocalciferol in Hemodialysis Patients." *Nephron Clin. Pract.*, 105:c132-c138 (2007).
Stamp et al., "Comparison of Oral 25-Hydroxycholecalciferol, Vitamin D, and Ultraviolet Light as Determinants of Circulating 25-Hydroxyvitamin D," *The Lancet*, 1341-1343 (Jun. 25, 1977).
Stein et al., "An Update on the Therapeutic Potential of Vitamin D Analogues," *Expert Opin. Investig. Drugs*, 12:825-840 (2003).
Stubbs et al., "Cholecalciferol supplementation alters calcitriol-responsive monocyte proteins and decreases inflammatory cytokines in ESRD," *J.Am.Soc.Nephrol.*, 21: 353-361 (2010).
Stumpf, "The Dose Makes the Medicine," *Drug Discovery Today*, 11:550-555 (2006).
Szycher, *Szycher's Dictionary of Biomaterials and Medical Devices*, pp. 20, 48, 127, Lancaster, Penn: Technomic Publishing Co., Inc. (1992).
Sömjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," *Steroids*, 63:340-343 (1998).
Taylor et al., "Interrelationship of Serum 25-Hydroxyvitamin $D_3$ and 1,25-Dihydroxyvitamin D in Juvenile Renal Osteodystrophy after Therapy with 25-Hydroxyvitamin $D_3$," *Metab. Bone Dis. & Rel. Res.*, 4:255-261 (1982).
Taylor et al., "The absence of 24,25-dihydroxycholecalciferol in anephric patients," *Clin.Sci.Mol.Med.Suppl.*, 55: 541-547 (1978).
Taylor, CM, 24,25-Dihydroxyvitamin D in Human Serum. In: Vitamin D. Basic Research and Clinical Applications, pp. 197-203. Walter de Gruyter, New York (1979).
Teitelbaum et al., "Calcifediol in Chronic Renal Insufficiency" *JAMA* 235(2):164-167 (1976).
Teitelbaum et al., "Tetracycline fluorescence in uremic and primary hyperparathyroid bone," *Kidney Int.*, 12:366-372 (1977).
Thomas et al., "Hypovitaminosis D in Medical Inpatients," *NEJM*, 338:777-783 (1998).

(56) References Cited

OTHER PUBLICATIONS

Thombre, "Assessment of the feasibility of oral controlled release in an exploratory development setting," *Drug Discovery Today*, 10(17): 1159-1166 (2005).
Tokmak et al., "High-dose cholecalciferol to correct vitamin D deficiency in haemodialysis patients," *Nephrol.Dial.Transplant.*, 23: 4016-4020 (2008).
Trakarnvanich et al., "Effect of high dose ergocalciferol in chronic kidney disease patients with 25-hydroxyvitamin D deficiency," *J.Med.Assoc.Thai.* 93: 885-891 (2010).
Van Weelden et al., "Apoptotic Regression of MCF-7 Xenografts in Nude Mice Treated with the Vitamin $D_3$ Analog, EB1089," *Endocrinology*, 139:2102-2110 (1998).
Verberckmoes et al., "Osteodystrophy of Dialysed Patients Treated with Vitamin D," *Proc Eur Dial Transplant Assoc.*, 10(0): 217-226 (1973).
Vieth, "What is the optimal vitamin D status for health?" *Prog. Biophys. Mol. Biol.*, 92:26-32 (2006).
Wise (ed.), *Handbook of Pharmaceutical Controlled Release Technology*, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).
Witmer et al., "Effects of 25-hydroxycholecalciferol on bone lesions of children with terminal renal failure" *Kidney International* 10:395-408 (1976).
Written Opinion for Application No. PCT/IB2008/003480, dated Mar. 31, 2009.
Written Opinion for Application No. PCT/US2007/061521, dated Jul. 17, 2007.
Written Opinion for Application No. PCT/US2008/061579, dated Aug. 21, 2008.
Zerwekh et al., "Extra-Renal Production of 24,25-Dihydroxyvitamin D in Chronic Renal Failure During 25 Hydroxyvitamin $D_3$ Therapy," *Kidney Int.*, 23:401-406 (1983).
Zisman et al., "Impact of Ergocalciferol Treatment of Vitamin D Deficiency on Serum Parathyroid Hormone Concentrations in Chronic Kidney Disease," *Am. J. Nephrol.*, 27:36-43 (2007).
Zucchelli et al., "Therapeutic effects of 25-hydroxycholecalciferol and sodium etidronate on renal osteodystrophy," *Mineral. Electrolyte Metab.* 7: 86-96 (1982).
Sitrin et al., Comparison of vitamin D and 25-hydroxyvitamin D absorption in the rat, Am. J. Physiol., 242(4):G326-32 (1982).
Holmberg et al., Absorption of a pharmacological dose of vitamin D3 from two different lipid vehicles in man: comparison of peanut oil and a medium chain triglyceride, Biopharm. Drug Dispos., 11(9):807-15(1990).
AlfaD$_3$® 0.25, 0.5 or 1 microgram Capsules (Alfacalcidol, Package Leaflet, Apr. 2010).
Alfarol® Capsules 3µg (Package Leaflet, Mar. 2011).
Ashford, Chapter 20: Bioavailability—physicochemical and dosage form factors, pp. 314-333 In: Aulton et al. (eds.), *Aulton's Pharmaceutics. The Design and Manufacture of Medicines,* Fourth Edition, Elsevier Publishing (2013).
Hectorol® (doxercalciferol) Capsules (Label, FDA, 2010).
Zemplar® (paricalcitol) Capsules, Final Agreed Upon Label (FDA, May 5, 2009).
Baez et al., Hipocalcemia severa posdenosumab, Nefrologfa (Madrid), 33(4): 614-615 (2013).
Baker et al., Plasma 25-hydroxy vitamin D concentrations in patients with fractures of the femoral neck, British Medical Journal, 1(6163):589 (1979).
Gradishar et al., Minimizing cancer's impacton bone with denosumab: current and future perspectives, Community oncology, 10(8):235-243 (2013).
Sirvent et al., Extreme hypocalcaemia and hyperparathyroidism following denosumab. Is this drug safe in chronic kidney disease?, Nefrologfa (Madrid), 34(4): 542-544 (2014).
9 Things That Can Undermine Your Vitamin D Level: Don't Let Your Vitamin D Absorption Slip Away, Harvard Health Publishing, downloaded from the Internet at: <https://www.health.harvard.edu/healthbeat/9-things-that-can-undermine-your-vitamin-d-level> (Feb. 11, 2019)., Feb. 11, 2019.
Albertson et al., Quantitative mapping of amplicon structure by array CGH identifies CYP24 as a candidate oncogene, Nat. Genet., 25(2):144-6 (2000).
Alvarez et al., "Vitamin D Supplementation in Pre-Dialysis Chronic Kidney Disease," Dermato-Endocrinology, 4(2):118-127 (2012).
Amin, The impact of improved phosphorus control: use of sevelamer hydrochloride in patients with chronic renal failure, Nephrol Dial Transplant, 17:340-345 (2002).
Anderson et al., Expression of VDR and CYP24A1 mRNA in human tumors, Cancer Chemother. Pharmacol., 57(2):234-40 (2006).
Anderson et al., Quantification of mRNA for the vitamin D metabolizing enzymes CYP27B1 and CYP24 and vitamin D receptor in kidney using real-time reverse transcriptase-polymerase chain reaction, 2003. J. Mol. Endoc 31:123-132.
Baggiolini et al., "Stereocontrolled Total Synthesis of 1 alpha, 25-Dihydroxycholecalciferol 1 and 1 alpha, 25-Dihydroxyergocalciferol," J. Org. Chem. 21: 3098-3108 (1986).
Berg et al., 24,25-Dihydroxyvitamin d3 and vitamin D status of community-dwelling black and white Americans, Clin. Chem., 61(6):877-84 (Jun. 2015).
Berruti et al., Prognostic role of serum parathyroid hormone levels in advanced prostate cancer patients undergoing zoledronic acid administration, Oncologist, 17(5):645-52 (2012).
Bertoldo et al., Serum 25-hydroxyvitamin D levels modulate the acute-phase response associated with the first nitrogen containing bisphosphonate infusion, J. Bone Miner. Res., 25(3):447-54 (Mar. 2010).
Bhatia et al., EB1089 inhibits the parathyroid hormone-related protein-enhanced bone metastasis and xenograft growth of human prostate cancer cells, Mol. Cancer Ther., 8(7):1787-98 (2009).
Binkley et al., "Laboratory Reporting of 25-Hydroxyvitamin D Results: Potential for Clinical Misinterpretation," Clinical Chemistry, 52(11);2124-2125 (2006).
BioTrends Research Group, TreatmentTrends (Registered): Nephrology (US) Q4 2014 (Dec. 2014).
Boudville et al., "Renal Function and 25-Hydroxyvitamin D Concentrations Predict Parathyroid Hormone Levels in Renal Transplant Patients," Nephrol Dial Transplant, 21:2621-2624 (2006).
Briese et al., "Arterial and cardiac disease in young adults with childhood-onset end-stage renal disease-impact of calcium and vitamin D therapy," Nephrology Dialysis Transplantation., 21:1906-1914 (2006).
Brodowicz et al., Early identification and intervention matters: A comprehensive review of current evidence and recommendations for the monitoring of bone health in patients with cancer, Cancer Treat Rev., 61:23-34 (2017).
Brown et al., "The Vitamin D Prodrugs 1 alpha(OH)D2, 1 alpha(OH)D3 and BCI-210 Suppress PTH Secretion by Bovine Parathyroid Cells," Nephrol Dial Transplant, 21:644-650 (2006).
Brown et al., "Vitamin D Analogues for Secondary Hyperparathyroidism," Nephrol Dial Transplant, 17[Suppl. 10]:10-19 (2002).
Cavalli et al., Biological effects of various regimes of 25-hydroxyvitamin D3 (calcidiol) administration on bone mineral metabolism in postmenopausal women, Clinical Cases in Mineral and Bone Metabolism, 6(2): 169-173 (2009).
Chapuy et al., Biochemical effects of calcium and vitamin D supplementation in elderly, institutionalized, vitamin D-deficient patients, Rev. Rhum. [Engl. Ed. 63 (2), 135-140), Feb. 1996.
Charnow, Novel Formulation Corrects Vitamin D, Lowers iPTH, Renal & Urology News (2012).
Chen et al., Safety of Denosumab Versus Zoledronic Acid in Patients with Bone Metastases: A Meta-Analysis of Randomized Controlled Trials, Oncol. Res. Treat., 39(7-9):453-9 (2016).
Chonchol et al., 25-Hydroxyvitamin D, insulin resistance, and kidney function in the Third National Health and Nutrition Examination Survey, Kidney Int., 71(2):134-9 (2007).
Coburn et al., "Doxercalciferol Safely Suppresses PTH Levels in Patients with Secondary Hyperparathyroidism Associated with Chronic Kidney Disease Stages 3 and 4," Am. J. Kidney Dis., 43(5):877-890 (2004).

(56) References Cited

OTHER PUBLICATIONS

Database WPI Week 199546 Thomson Scientific, London, GB; AN 1995-355178 XP002464406.
Database WPI Week 199546 Thomson Scientific, London, GB; An 1995-355178 XP002680886.
El Abdaimi et al., Reversal of hypercalcemia with the vitamin D analogue EB1089 in a human model of squamous cancer, Cancer Res., 59(14):3325-8 (1999).
Ennis et al., Current recommended 25-hydroxyvitamin D targets for chronic kidney disease management may be too low, J. Nephrol., 29(1):63-70 (Feb. 2016).
Epps et al., "Vitamin D Metabolism: Implications for Treatment in Oncology," Oncology News, 4:42-44 (2009).
Final Office Action, U.S. Appl. No. 16/089,235, dated Dec. 10, 2019, 35 pages.
Fliser et al., Fibroblast gowth factor 23 (FGF23) predicts progression of chronic kidney disease: the mild to moderate kidney disease (MMKD) study, J. Am. Soc. Nephrol., 18:2601-8 (2007).
Fournier et al., "Impact of calcium and vitamin D therapy on arterial and cardiac disease in young adults with childhood-onset and stage renal disease," Nephrol Dial Transplant, 22:956-957 (2006).
Friedrich et al., Analysis of the vitamin D system in cervical carcinomas, breast cancer and ovarian cancer, Recent Results Cancer Res., 164:239-46 (2003).
Fritsche et al., "Regulation of 25-Hydroxyvitamin D3-1α-Hydroxylase and Production of 1α,25-Dihydroxyvitamin D3 by Human Dendritic Cells," Blood, 102(9):3314-3316 (2003).
Fukagawa et al., FGF23: its role in renal bone disease, Pediatr. Nephrol., 21:1802-6 (2006).
Fukagawa et al., With or without the kidney: the role of FGF23 in CKD, Nephrol. Dial. Transplant., 20:1295-8 (2005).
Gal-Moscovici et al., Role of vitamin D deficiency in chronic kidney disease, Journal of Bone and Mineral Res. 22:V91-V94 (2007).
Garland et al., Vitamin D for cancer prevention: global perspective, Ann. Epidemiol., 19(7):468-83 (2009).
Gibson, ed., Product optimisation. Pharmaceutical Preformulation and Formulation: A Practical Guide from Candidate Drug Selection to Commercial Dosage Form, 295-8 (2004).
Gomez-Alonso et al., "Vitamin D Status and Secondary Hyperparathyroidism: The Importance of 25-Hydroxyvitamin D Cut-Off Levels," Kidney International, 63(Supp. 85):S44-S48 (2003).
Gopinath et al., Disintegrants—A Brief Review, J. Chem. Pharm. Sci., 5(3):105-12 (Jul.-Sep. 2012).
Granja et al., "Studies on the Opening of Dioxanone and Acetal Templates and Application to the Synthesis of 1 alpha, 25-Dihydroxyvitamin D21," J. Org. Chem., 58:124-131 (1993).
Haddad et al., "Vitamin D Plasma Binding Protein. Turnover and Fate in the Rabbit," J. Clin. Invest., 67(5):1550-1560 (1981).
Harris R Z et al: "Pharmacokinetics of cinacalcet hydrochloride when administered with ketoconazole", Clinical Pharmacokinetics, Adis International Ltd., Auckland, NZ, vol. 46, No. 6, Jan. 1, 2007 (Jan. 1, 2007), pp. 495-501.
Helvig et al., Dysregulation of renal vitamin D metabolism in the uremic rat, Kidney Int., 78(5):463-72 (2010).
Hemodialysis (2015, 4 pages, Accessed from https://www.kidney.org/atoz/content/hemodialysis on Jun. 19, 2019) (Year: 2015).
Henry et al., Response of chick parathyroid glands to the vitamin D metabolites, 1,25-dihydroxycholecalciferol and 24,25-dihydroxycholecalciferol, J. Nutr., 107(10):1918-26 (1977).
Hidroferol (Registered) (calcifediol): Casos de Hipercalcemia e Hipervitaminosis D, Butlleti de Farmacovigilancia de Catalunya, 9(5):17-20 (2011).
Holick et al., Evaluation, treatment, and prevention of vitamin D deficiency: an Endocrine Society clinical practice guideline, J. Clin. Endocrinol. Metab., 96(7):1911-30 (Jul. 2011).
Holick, Vitamin D for health and in chronic kidney disease, Semin. Dial., 18(4):266-75 (2005).

Sato et al., Increased 1,25-(OH)2D2 concentration in a patient with malignancy-associated hypercalcemia receiving intravenous hyperalimentation inadvertently supplemented with vitamin D2, Intern. Med., 32(11)1886-90 (1993).
Schmidt, "Measurement of 25-Hydroxyvitamin D Revisited," Clinical Chemistry, 52(12):2304-2305 (2006).
Schwartz et al., Extended-release calcifediol (ERC) effectively increased serum 25-hydroxyvitamin D levels in breast and prostate cancer patients without significant impact on serum calcium or phosphorus, Opko Renal (2018).
Sebert et al. "Comparative effects of equal doses of vitamin D2 and vitamin D3 for the correction of vitamin D deficiency in the elderly" in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Segersten et al.: Potentiating effects of nonactive/active vitamin D analogues and ketoconazole in parathyroid cells, Clinical Endocrinology., vol. 66, No. 3, Mar. 1, 2007 (Mar. 1, 2007), pp. 399-404.
Sensipar (cinacalcet) prescriptioninformation, revised Aug. 2011.
Sensipar package insert (Year: 2004).
Shi et al., "Preparation of Chitosan/Ethylcellulose Complex Microcapsule and its Application in Controlled Release of Vitamin D2," Biomaterials, 23:4469-4473 (2002).
Sicinski et al., "Synthesis of 1 alpha, 25-Dihydroxyvitamin D2, Its 24 Epimer and Related Isomers, and Their Binding Affinity for the 1, 25-Dihydroxyvitamin D3 Receptor," Bioorganic Chemistry, 13:158-169 (1985).
Singh et al., "C-3 Epimers Can Account for a Significant Proportion of Total Circulating 25-Hydroxyvitamin D in Infants, Complicating Accurate Measurement and interpretation of Vitamin D Status," J. Clin. Endo. & Metabol., 91(8):3055-3061 (2006).
Skugor M. et al.: Évolution and current state of assays for parathyriod hormone, Biochemia Medica, vol. 20, No. 2, 2010, pp. 221-228.
Slatopolsky et al., "Differential Effects of 19-nor-1,25-(OH)2D2 and 1α-Hydroxyvitamin D2 on Calcium and Phosphorus in Normal and Uremic Rats," Kidney International, 62:1277-1284 (2002).
Sosa et al., "The Effect of 25-dihydroxyvitamin D on the Bone Mineral Metabolism of Elderly Women with Hip Fracture," Rheumatology, 39:1263-1268 (2000).
Soyfoo et al., Non-malignant causes of hypercalcemia in cancer patients: a frequent and neglected occurrence, Support Care Cancer, 21(5):1415-9 (2013).
Sprague et al., Modified-release calcifediol effectively controls secondary hyperparathyroidism associated with vitamin D insufficiency in chronic kidney disease, Am. J. Nephrol., 40(6):535-45 (2015).
Sprague et al., Use of Extended-Release Calcifediol to Treat Secondary Hyperparathyroidism in Stages 3 and 4 Chronic Kidney Disease, Am. J. Nephrol., 44(4):316-25 (2016).
Stamp, "Intestinal Absorption of 25-hydroxycholecalciferol," The Lancet, 121-123 (1974).
Stavroulopoulos et al., Relationship between vitamin D status, parathyroid hormone levels and bone mineral density in patients with chronic kidney disease stages 3 and 4, Nephrology (Carlton), 13(1):63-7 (Feb. 2008).
Tamez et al., Vitamin D reduces left atrial volume in patients with left ventricular hypertrophy and chronic kidney disease, Am. Heart J., 164(6):902-9.e2 (Dec. 2012).
Tebben et al., Elevated fibroblast growth factor 23 in women with malignant ovarian tumors, Mayo Clin. Proc., 80:745-51 (2005).
Terrie, Monitoring Combination Drug Therapy, Pharmacy Times, published Jan. 18, 2010., Jan. 19, 2010.
Tomida et al., Serum 25-hydroxyvitamin D as an independent determinant of 1-84 PTH and bone mineral density in non-diabetic predialysis CKD patients, Bone, 44(4):678-83 (Apr. 2009).
Tsuji, et al. "A New and Convenient Synthesis of 1α,25-Dihydroxyvitamin D2 and It 24R-Epimer," Bull. Chem. Soc. Jpn., 62:10 pp. 3132-3137 (1989).
Tuohimaa et al., "Both High and Low Levels of Blood Vitamin D are Associated with a Higher Prostate Cancer Risk: A Longitudinal, Nested Case-Control Study in the Nordic Countries," Int. J. Cancer, 108(1):104-108 (2004).

(56) References Cited

OTHER PUBLICATIONS

US FDA Clinical Review and Evaluation of NDA for Calderol (Registered) calcifediol capsules (believed to be available circa 1983).
US FDA Summary of Basis of Approval for Calderol (Registered) calcifediol capsules (believed to be available circa 1980).
Vieth, "Vitamin D Supplementation, 25-Hydroxyvitamin D Concentrations, and Safety," Am. J. Clin. Nutr., 69:842-856 (1999).
Wagner et al., The ratio of serum 24,25-dihydroxyvitamin D(3) to 25-hydroxyvitamin D(3) is predictive of 25-hydroxyvitamin D(3) response to vitamin D(3) supplementation, J. Steriod Biochem. Mol. Biol., 126(3-5):72-7 (Sep. 2011).
Wang-Gillam et al., Evaluation of vitamin D deficiency in breast cancer patients on bisphosphonates, Jul. 1, 2008, Oncologist, 821-7, 13(7).
Wootton, "Improving the Measurement of 25-Hydroxyvitamin D," Clin Biochem Rev, 26:33-36 (2005).
Yanoff et al., "The Prevalence of Hypovitaminosis D and Secondary Hyperparathyroidism in Obese Black Americans," Clin. Endocrinol. (Oxf), 64(5):523-529 (2006).
Yueh-Ting et al: Comparison between Calcitriol and Caltiriol Plus Low-Dose Cinacalcet for the Treatment of Moderate to Severe Secondary Hyperparathyroidism in Nutrients, vol. 5, No. 4, Apr. 19, 2013 (Apr. 19, 2013), pp. 1336-1348.
Zerwekh et al (Extra-renal production of 24, 25-dihydroxyvitamin D in chronic renal failure during 25 hydroxyvitamin D3 therapy, Kidney International, vol. 23, (1983), pp. 401-406).
Zerwekh J. E.: "Blood biomarkers of vitamin D status", The American Journal of Clinical Nutrition, vol. 87Suppl., 2008, pp. 1087S-1091S.
Zuradelli et al., High incidence of hypocalcemia and serum creatinine increase in patients with bone metastases treated with zoledronic acid, Oncologist, 14(5):548-56 (2009).
Ibrahim et al., Serum fibroblast growth factor-23 levels in chronic haemodialysis patients, Int. Urol. Nephrol., 41:163-9 (2009).
Inoue et al., Role of the vitamin D receptor in FGF23 action on phosphate metabolism, Biochem. J., 399:325-31 (2005).
International Preliminary Report on Patentability for Corresponding International Application No. PCT/US09/39355, dated Oct. 14, 2010, 8 pages.
Jones et al., Cytochrome P450-mediated metabolism of vitamin D, J. Lipid Res., 55(1):13-31 (2014).
Kaufmann et al., Clinical utility of simultaneous quantitation of 25-hydroxyvitamin D and 24,25-dihydroxyvitamin D by LC-MS/MS involving derivatization with DMEQ-TAD, J. Clin. Endocrinol. Metab., 99(7):2567-74 (Jul. 2014).
Kazama et al., Role of circulating fibroblast growth factor 23 in the development of secondary hyperparathyroidism, Ther. Apher. Dial., 9:328-30 (2005).
KDOQI Clinical practice guidelines 2004. National Kidney Foundation).
Khachane et al., "Novel Suatained Release Drug Delivery System: Review," IJPRD, 3(12):1-14 (2012).
Kidney Disease Improving Global Outcomes (KDIGO) 2017 Clinical Practice Guideline Update for the Diagnosis, Evaluation, Prevention, and Treatment of Chronic Kidney Disease—Mineral and Bone Disorder (CKD-MBD). Kidney Int Suppl. 2017;7(1):1-59.
Kidney Disease Improving Global Outcomes (KDIGO) Clinical Practice Guidelines for Diagnosis, Evaluation, Prevention, and Treatment of Chronic Kidney Disease—Mineral and Bone Disorder (CKD-MBD), Kidney International Supplement, 113:S1-130 (2009).
Kinoshita et al., "1,25-Dihydroxyvitamin D Suppresses Circulating Levels of Parathyroid Hormone in a Patient with Primary Hyperparathyroidism and Coexistent Sarcoidosis," J. Clin. Endo. & Metabol., 90(12):6727-6731 (2005).
Kobayashi et al., "Variation of 25-Hydroxyvitamin D3 and 25-Hydroxyvitamin D2 Levels in Human Plasma Obtained from 758 Japanese Healthy Subjects," J. Nutr. Sci. Vitaminol (Tokyo), 29(3):271-281 (1983). Abstract Only.

Kovesdy et al., Association of activated vitamin D treatment and mortality in chronic kidney disease, Arch. Intern. Med., 168(4):397-403 (Feb. 2008).
Krishnan et al., The role of vitamin D in cancer prevention and treatment, Rheum. Dis. Clin. North Am., 38(1):161-78 (2012).
KURO-O, Klotho in chronic kidney disease—what's new?, Nephrol. Dial. Transplant., 4 pp. (2009).
Lo et al., Vitamin D absorption in healthy subjects and in patients with intestinal malabsorption syndromes, Am. J. Clin. Nutr., 42(4):644-9 (1985).
Luo et al., 24-Hydroxylase in cancer: impact on vitamin D-based anticancer therapeutics, J. Steroid Biochem. Mol. Biol., 136:252-7 (2013).
M. Larrosa et al. (Abstract FR10365, Long term treatment of Hypovitaminisis, clacidiol or cholecalcidiol).
Martin et al., "19-Nor-1-alpha-25-Dihydroxyvitamin D2 (Paricalcitol) Safely and Effectively Reduces the Levels of Intact Parathyroid Hormone in Patients on Hemodialysis," J. Am. Soc. Nephrol., 9:1427-1432 (1998).
Martin-Baez et al., Severe hypocalcaemia post-denosumab, Nefrologia, 33(4):614-5 (2013).
Melanie S Joy Pharmd FCCP et al: "Outcomes of Secondary Hyperparathyroidism in Chronic Kidney Disease and the Direct Costs of Treatment", Journal of Managed Care Pharmacy, Academy of, Managed Care Pharmacy, Alexandria, VA, vol. 13, No. 5, Jan. 1, 2007 (Jan. 1, 2007), pp. 397-411.
Mimori et al., Clinical significance of the overexpression of the candidate oncogene CYP24 in esophageal cancer, Ann. Oncol., 15(2):236-41 (2004).
Modem Pharmaceutics 4th ed., Marcel Dekker, Inc., New York, NY, p. 16-21 (2002).
Morris, "Cats Discriminate Between Cholecalciferol and Ergocalciferol," J. Anim. Physiol, a. Anim. Nutr., 86:229-238 (2002).
Motellon et al., Parathyroid hormone-related protein, parathyroid hormone, and vitamin D in hypercalcemia of malignancy, Clin. Chim. Acta, 290(2):189-97 (2000).
NASMHPD Medical Director's Technical Report on Psychiatric Polypharmacy, Sep. 2001.
National Kidney Foundation Guidelines, NKF, Am. J. Kidney Dis., 42(4,Suppl 3):S1-S202 (2003).
NewsWire (https://www.newswire.ca/news-releases/cytochroma-announces-data-presentations-at-american-society-of-hephrologys43rd-annual-meeting-and-scientific-exposition-546289852.html, published Nov. 18, 2010) (Year: 2010).
Non-Final Office Action received for U.S. Appl. No. 12/597,230, dated Dec. 13, 2019, 15 pages.
Olmos et al., Effects of 25-hydroxyvitamin D3 therapy on bone turnover markers and PTH levels in postmenopausal osteoporotic women treated with alendronate, J. Clin. Endocrinol. Metab., 97(12):4491-7 (2012).
OPKO Health Inc., Safety/Efficacy Study of CTAP101 in Chronic Kidney Disease Subjects With Secondary Hyperparathyroidism (SHPT), <https://clinicaltrials.gov/ct2/show/NCT01219855> Oct. 13, 2010.
Package insert for Hectorol (doxercalciferol capsules), Genzyme (2011).
Package insert for Zemplar (paricalcitol) Capsules, Abbott (2011).
Pak et al., "Treatment of Vitamin D-Resistant Rickets With 25-Hydroxycholecalciferol," Arch Intern Med, 129:894-899 (1972).
Parise et al., CYP24, the enzyme that catabolizes the antiproliferative agent vitamin D, is increased in lung cancer, Int. J. Cancer, 119(8):1819-28 (2006).
Patel et al., "Glomerular Filtration Rate is a Major Determinant of the Relationship Between 25-Hydroxyvitamin D and Parathyroid Hormone," Calcif. Tissue Int., 80:221-226 (2007).
Perrie, Pharmaceutics: Drug Delivery and Targeting, Second Edition, Chapter 1 (2012).
Petkovich et al., "CYP24A1 and Kidney Disease," Current Opin. in Nephrology and Hypertension, 20:337-344 (2011).
Posner et al., "Vitamin D Analogues Targeting CYP24 in Chronic Kidney Disease," J. Steroid Biochem and Mol. Biol., 121:13-19 (2010).

(56) References Cited

OTHER PUBLICATIONS

Prescribing Information for Calderol (Registered) calcifediol capsules (1988).
Prescribing Information for Hectorol (Registered) (doxercalciferol capsules), Genzyme (2011).
Prescribing information for Zemplar (Registered) (paricalcitol) Capsules, Abbott (2011).
Querfeld et al., Vitamin D deficiency and toxicity in chronic kidney disease: in search of the therapeutic window, Pediatr. Nephrol., 25(12):2413-30 (Dec. 2010).
Rabbani, Molecular mechanism of action of parathyroid hormone related peptide in hypercalcemia of malignancy: therapeutic strategies (review), Int. J. Oncol., 16(1):197-206 (2000).
Rambeck et al., "Biological Activity of 1 alpha,25-Dihydroxyergocalciferol in Rachitic Chicks and in Rats," IZVIAK, 54(2/3):135-139 (1984).
Ravani et al., Vitamin D levels and patient outcome in chronic kidney disease, Kidney Int., 75(1):88-95 (Jan. 2009).
Richard et al., PTHrP gene expression in cancer: do all paths lead to Ets?, Crit. Rev. Eukaryot. Gene Expr., 15(2):115-32 (2005).
Rix et al., "Effect of 18 Months of Treatment with Alfacalcidol on Bone in Patients with Mild to Moderate Chronic Renal Failure," Nephrol Dial Transplant, 19:870-876 (2004).
Saseen et al., "Dual calcium-channel blocker therapy in the treatment of hypertension," Ann Pharmacother., 30(7-8): 802-10 (1996).

* cited by examiner

METHOD OF TREATING VITAMIN D INSUFFICIENCY AND DEFICIENCY

CROSS-REFERENCE TO RELATED APPLICATION

The benefit under 35 U.S.C. § 119(e) of U.S. Provisional Patent Application Ser. No. 60/913,849 filed Apr. 25, 2007, is hereby claimed.

FIELD OF DISCLOSURE

The disclosure relates generally to methods and dosage forms for reducing toxicity associated with treatment using vitamin $D_3$, the pro-hormone 25-hydroxyvitamin $D_3$, active hormone 1,25-dihydroxyvitamin $D_3$ or vitamin $D_3$ analogs (including hydroxy and dihydroxy forms).

BACKGROUND

The Vitamin D metabolites known as 25-hydroxyvitamin $D_2$ and 25-hydroxyvitamin $D_3$ (collectively referred to as "25-hydroxyvitamin D") are fat-soluble steroid prohormones to Vitamin D hormones that contribute to the maintenance of normal levels of calcium and phosphorus in the bloodstream. The prohormone 25-hydroxyvitamin $D_2$ is produced from Vitamin $D_2$ (ergocalciferol) and 25-hydroxyvitamin $D_3$ is produced from Vitamin $D_3$ (cholecalciferol) primarily by one or more enzymes located in the liver. The two prohormones can also be produced outside of the liver from Vitamin $D_2$ and Vitamin $D_3$ (collectively referred to as "Vitamin D") in certain cells, such as enterocytes, which contain enzymes identical or similar to those found in the liver.

The prohormones are further metabolized in the kidneys into potent hormones. The prohormone 25-hydroxyvitamin $D_2$ is metabolized into a hormone known as 1α,25-dihydroxyvitamin $D_2$; likewise, 25-hydroxyvitamin $D_3$ is metabolized into 1α,25-dihydroxyvitamin $D_3$ (calcitriol). Production of these hormones from the prohormones can also occur outside of the kidney in cells which contain the required enzyme(s).

The Vitamin D hormones have essential roles in human health which are mediated by intracellular Vitamin D receptors (VDR). In particular, the Vitamin D hormones regulate blood calcium levels by controlling the absorption of dietary calcium by the small intestine and the reabsorption of calcium by the kidneys. Excessive hormone levels, whether transient or prolonged, can lead to abnormally elevated urine calcium (hypercalciuria), blood calcium (hypercalcemia), and blood phosphorus (hyperphosphatemia). The Vitamin D hormones also participate in the regulation of cellular differentiation and growth, parathyroid hormone (PTH) secretion by the parathyroid glands, and normal bone formation and metabolism. Further, Vitamin D hormones are required for the normal functioning of the musculoskeletal, immune, and renin-angiotensin systems. Numerous other roles for Vitamin D hormones are being postulated and elucidated, based on the documented presence of intracellular VDR in nearly every human tissue and the variety of vitamin D responsive genes.

The actions of Vitamin D hormones on specific tissues depend on the degree to which they bind to (or occupy) the intracellular VDR in those tissues. The prohormones 25-hydroxyvitamin $D_2$ and 25-hydroxyvitamin $D_3$ have essentially identical affinities for the VDR which are estimated to be at least 100-fold lower than those of the Vitamin D hormones. As a consequence, physiological concentrations of 25-hydroxyvitamin $D_2$ and 25-hydroxyvitamin $D_3$ have little, if any, biological actions without prior metabolism to Vitamin D hormones. However, supraphysiologic levels of 25-hydroxyvitamin $D_2$ and 25-hydroxyvitamin $D_1$, in the range of 10 to 1,000 fold higher than normal, may sufficiently occupy the VDR to exert actions like the Vitamin D hormones.

Blood levels of both the prohormones and the Vitamin D hormones are normally constant throughout the day, given a sustained, adequate supply of Vitamin D from sunlight exposure or an unsupplemented diet. Blood levels of 25-hydroxyvitamin D, however, can increase markedly after administration of currently available Vitamin D supplements, especially at doses which greatly exceed the minimum amounts required to prevent Vitamin D deficiency, rickets, or osteomalacia. Prohormone blood levels can also increase markedly after rapid intravenous administration of 25-hydroxyvitamin $D_2$ or 25-hydroxyvitamin $D_3$, or after administration of immediate release forms of these compounds.

Production of 25-hydroxyvitamin $D_2$ and 25-hydroxyvitamin $D_3$ declines when Vitamin D is in short supply, as in conditions such as Vitamin D insufficiency or Vitamin D deficiency (alternatively, hypovitaminosis D). Low production of 25-hydroxyvitamin $D_2$ and 25-hydroxyvitamin $D_3$ leads to low blood levels of 25-hydroxyvitamin D. Inadequate Vitamin D supply often develops in individuals who are infrequently exposed to sunlight, have chronically inadequate intakes of Vitamin D, or suffer from conditions or clinical procedures, such as bariatric surgery, that result in reduced intestinal absorption of fat soluble vitamins (such as Vitamin D). It has recently been reported that most individuals living in northern latitudes have inadequate Vitamin D supply. Left untreated, inadequate Vitamin D supply can cause serious bone disorders, including rickets and osteomalacia, and may contribute to the development of many other disorders including osteoporosis, non-traumatic fractures of the spine and hip, obesity, diabetes, muscle weakness, immune deficiencies, autoimmune disorders, hypertension, psoriasis, and various cancers.

The Institute of Medicine (IOM) of the National Academy of Sciences has concluded that an Adequate Intake (AI) of Vitamin D for a healthy individual ranges from 200 to 600 IU per day, depending on the individual's age and sex [Standing Committee on the Scientific Evaluation of Dietary Reference Intakes, Dietary reference intakes: calcium, phosphorus, magnesium, vitamin D, and fluoride. Washington, D.C.: National Academy Press (1997)], incorporated by reference.] The AI for Vitamin D was defined primarily on the basis of a serum 25-hydroxyvitamin D level sufficient to prevent Vitamin D deficiency, rickets or osteomalacia (or at least 11 ng/mL). The IOM also established a Tolerable Upper Intake Level (UL) for Vitamin D of 2,000 IU per day, based on evidence that higher doses are associated with an increased risk of hypercalciuria, hypercalcemia and related sequelae, including cardiac arrhythmias, seizures, and generalized vascular and other soft-tissue calcification.

Currently available oral Vitamin $D_3$ supplements are far from ideal for safely achieving and maintaining optimal blood 25-hydroxyvitamin D levels. These preparations typically contain 400 IU to 5,000 IU of Vitamin $D_3$ and are formulated for quick or immediate release in the gastrointestinal tract. When administered at chronically high doses, as is often required for Vitamin D repletion, these products may cause toxicity.

Vitamin $D_3$ supplementation above the UL is frequently needed in certain individuals; however, currently available oral Vitamin $D_3$ supplements are not well suited for maintaining blood 25-hydroxyvitamin $D_3$ levels at optimal levels given the problems of administering high doses of Vitamin D compounds which may give rise to toxicity.

Administration of 25-hydroxyvitamin $D_3$ can produce surges or spikes in blood and intracellular 25-hydroxyvitamin D levels, thereby promoting toxicity manifesting as hypercalcemia and hypercalciuria.

Clearly, alternative approaches to Vitamin D supplementation are needed given the safety problems encountered with currently available oral Vitamin D supplements.

SUMMARY OF THE INVENTION

The present invention relates generally to methods for effectively and safely restoring blood 25-hydroxyvitamin D to optimal levels (defined for patients as >30 ng/mL 25-hydroxyvitamin D, or >75 nmol/L) and maintaining blood 25-hydroxyvitamin D levels at such optimal levels, methods for preventing the drop of blood 25-hydroxyvitamin D levels below such optimal levels, and methods for preventing or treating secondary hyperparathyroidism.

Excessive elevation of serum 25-hydroxyvitamin $D_3$ can give rise to toxicity. One manifestation of such toxicity is attributable to elevated serum calcium levels, including cardiac arrhythmias, seizures, and generalized vascular and other soft-tissue calcification. The present invention is based on the demonstration that toxicity associated with treatment using the pro-hormone 25-hydroxyvitamin $D_3$ can be reduced or eliminated by co-administration of 25-hydroxyvitamin $D_2$. The invention is also based on the concept that co-administration of 25-hydroxyvitamin $D_3$ along with 25-hydroxyvitamin $D_2$ can more effectively elevate serum levels of 25-hydroxyvitamin D without causing toxicity than administration of either alone.

The invention thus relates to methods, compositions, dosage forms, and kits that can be used to restore serum 25-hydroxyvitamin D levels to normal (at least 30 ng/ml) or higher than normal levels in a safe and effective manner, to prevent the occurrence or severity of subnormal levels of serum 25-hydroxyvitamin D, and/or to prevent or treat secondary hyperparathyroidism.

In one aspect, the methods of the invention include dosing a subject, an animal or a human patient, with a sufficient amount of one or more vitamin $D_2$ supplements to reduce vitamin D toxicity associated with administration of one or more vitamin $D_3$ supplements. In exemplary embodiments, the vitamin $D_3$ supplement referred to herein is vitamin $D_3$ (cholecalciferol), 25-hydroxyvitamin $D_3$, 1α,25-dihydroxyvitamin $D_3$, or a vitamin $D_3$ analog (including all known hydroxy and dihydroxy forms), including, 1,25-dihydroxy-19-nor-vitamin $D_3$, 1α-hydroxyvitamin $D_3$, and other compounds known in the art. In exemplary embodiments, the vitamin $D_2$ supplement referred to herein is ergocalciferol or 25-hydroxyvitamin $D_2$ or 1,25-dihydroxyvitamin $D_2$, and other compounds known in the art.

The one or more vitamin $D_2$ supplements may be administered separately or in some combination during a course of treatment; similarly, the one or more vitamin $D_3$ supplements may be administered separately or in some combination during a course of treatment. Preferably, the vitamin $D_3$ supplement is administered in a therapeutically effective amount (e.g., amount effective to prevent or treat hypovitaminosis D and/or secondary hyperparathyroidism), while the vitamin $D_2$ supplement is administered in an amount effective to reduce vitamin D toxicity. In some embodiments, administration of the vitamin $D_2$ supplement permits administration of the vitamin $D_3$ supplement in an amount that would normally be expected to result in adverse effects or toxicity. The vitamin $D_2$ supplement and vitamin $D_3$ supplement can be administered by the same or different routes, e.g. oral, intravenous, topical, intraperitoneal and/or transdermal and in the same or different compositions. The vitamin $D_2$ supplement and vitamin $D_1$ supplement can be administered at the same time, or at different but overlapping times during a course of treatment (e.g., on alternating days or at different times in the same day). Preferably, the vitamin $D_2$ supplement and vitamin $D_3$ supplement are administered on the same day.

In exemplary embodiments, the ratio (by weight or molarity) of vitamin $D_3$ supplement to vitamin $D_2$ supplement can range from 100:1 to 1:20, e.g. 75:1, 60:1, 50:1, 40:1, 30:1, 20:1, 15:1, 10:1, 5:1, 4:1, 3:1, 2:1, 1.5:1, 1:1, 1:2, 1:3, 1:4, 1:5, 1:10, or 1:15. While ratios tested herein were ratios measured by weight, the molecular weight of the $D_2$ and $D_3$ compounds tested is similar; it is expected that the activity is on a molar basis and thus the results apply similarly to ratios measured by molarity.

In another aspect, the methods of the invention involve providing a vitamin $D_3$ supplement to a patient, optionally in a therapeutically effective amount, and informing the patient that adverse effects related to administration of such vitamin $D_3$ supplement can be reduced by co-administration of a vitamin $D_2$ supplement.

In one exemplary embodiment, the method involves co-administering a combination of 25-hydroxyvitamin $D_3$ and 25-hydroxyvitamin $D_2$ in a single combined formulation, or in two separate formulations through various routes including, intravenous, oral, topical, intraperitoneal and transdermal. In a related embodiment, the 25-hydroxyvitamin $D_3$ is administered in a therapeutically effective amount to raise serum 25-hydroxyvitamin D levels, preferably to raise 25-hydroxyvitamin $D_3$ levels to 30 ng/mL or higher, and the 25-hydroxyvitamin $D_2$ is administered in a toxicity-reducing amount. Co-administration of 25-hydroxyvitamin $D_3$ along with an amount of 25-hydroxyvitamin $D_2$ can effectively elevate serum 25-hydroxyvitamin D levels with a significantly reduced level of toxicity or a lower risk of toxicity as compared to the administration of 25-hydroxyvitamin $D_3$ alone. Thus, serum levels of 25-hydroxyvitamin D can be raised more rapidly and safely, and/or higher amounts of 25-hydroxyvitamin $D_3$ can be administered.

In another embodiment, this invention provides methods for co-administration of ergocalciferol and cholecalciferol that will have safety advantages compared to the administration of cholecalciferol alone.

In another embodiment, this invention provides methods for co-administering 25-hydroxyvitamin $D_3$ along with ergocalciferol or, co-administering cholecalciferol along with 25-hydroxyvitamin $D_2$.

In the methods of the invention, doses of vitamin $D_2$ supplement and vitamin $D_3$ supplement are administered together or separately within a time frame in which their administration achieves the safety benefit described in this invention. For example, 25-hydroxyvitamin $D_2$ may be administered at one hour before, 6 hours before, 12 hours before, 24 hours before or 2 days before administration of 25-hydroxyvitamin $D_3$. Conversely, 25-hydroxyvitamin $D_3$ may be administered at one hour before, 6 hours before, 12 hours before, 24 hours before or 2 days before administration of 25-hydroxyvitamin $D_2$. Alternatively, the patient may be given instructions to take 25-hydroxyvitamin $D_3$ one, two or three times per week and 25-hydroxyvitamin $D_2$ one, two or three times per week, so long as each vitamin $D_2$ supplement and vitamin $D_3$ supplement is taken at least once (or twice or three times) per week. 25-hydroxyvitamin $D_2$ and 25-hydroxyvitamin $D_3$ or combinations thereof, optionally with other therapeutic agents, can be administered in accordance with the above described embodiments in cumulative dosage amounts of from about 1 to 100 μg per day, with the preferred dosage amounts of from about 5 to 50 μg per day, for example about 10 to 25 μg.

In another related aspect, the invention provides compositions that contain both a vitamin $D_2$ supplement and a vitamin $D_3$ supplement. In some embodiments, the vitamin $D_3$ supplement is present in a therapeutically effective amount while the vitamin $D_2$ supplement is present in a toxicity-reducing amount. In some embodiments, the vitamin $D_3$ supplement is present at an amount that, if given alone, would be expected to result in adverse effects or toxicity. The compositions may comprise any of the vitamin $D_2$ supplements and/or vitamin $D_3$ supplements described above, in any of the ratios described above. In exemplary embodiments, the compositions are a cumulative unit dose (total amount of 25-hydroxyvitamin $D_2$ and 25-hydroxyvitamin $D_3$ together) ranging from about 1 to 100 μg per unit dose, e.g. about 10, 25, 50, 75 or 100 μg per unit dose. In other exemplary embodiments, the compositions are a unit dose containing about 10, 25, 50, 75 or 100 μg of 25-hydroxyvitamin $D_3$, and an additional toxicity-reducing amount of 25-hydroxyvitamin $D_2$.

In an exemplary embodiment, an amount of 25-hydroxyvitamin $D_2$ along with 25-hydroxyvitamin $D_3$ is included in a formulation and is orally administered daily to a human or animal in need of treatment. In another embodiment, an amount of 25-hydroxyvitamin $D_2$ and 25-hydroxyvitamin $D_3$ is included in an isotonic sterile formulation suitable for intravenous administration, and is gradually injected thrice weekly into a human or animal in need of treatment.

In yet another aspect, the kits of the invention comprise a container comprising a vitamin $D_3$ supplement, optionally in a therapeutically effective amount, with labeling instructions informing the patient that adverse effects related to administration of such vitamin $D_3$ supplement can be reduced by co-administration of a vitamin $D_2$ supplement. The kits can further comprise a vitamin $D_2$ supplement, optionally in toxicity-reducing amount.

The foregoing brief description has outlined, in general, the featured aspects of the invention and is to serve as an aid to better understanding the more complete detailed description which is to follow. In reference to such, there is to be a clear understanding that the present invention is not limited to the method or detail of manufacture, chemical composition, or application of use described herein. Any other variation of manufacture, chemical composition, use, or application should be considered apparent as an alternative embodiment of the present invention. Other advantages and a fuller appreciation of the specific adaptations, compositional variations and chemical and physical attributes of this invention will be gained upon examination of the detailed description.

Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

BRIEF DESCRIPTION OF THE DRAWINGS

In FIG. 1, * signifies P<0.05,  signifies P<0.001 and * signifies P<0.0001 statistical significance.

In FIG. 3, * signifies P<0.05 statistical significance.

DETAILED DESCRIPTION OF THE INVENTION

Figure 1:
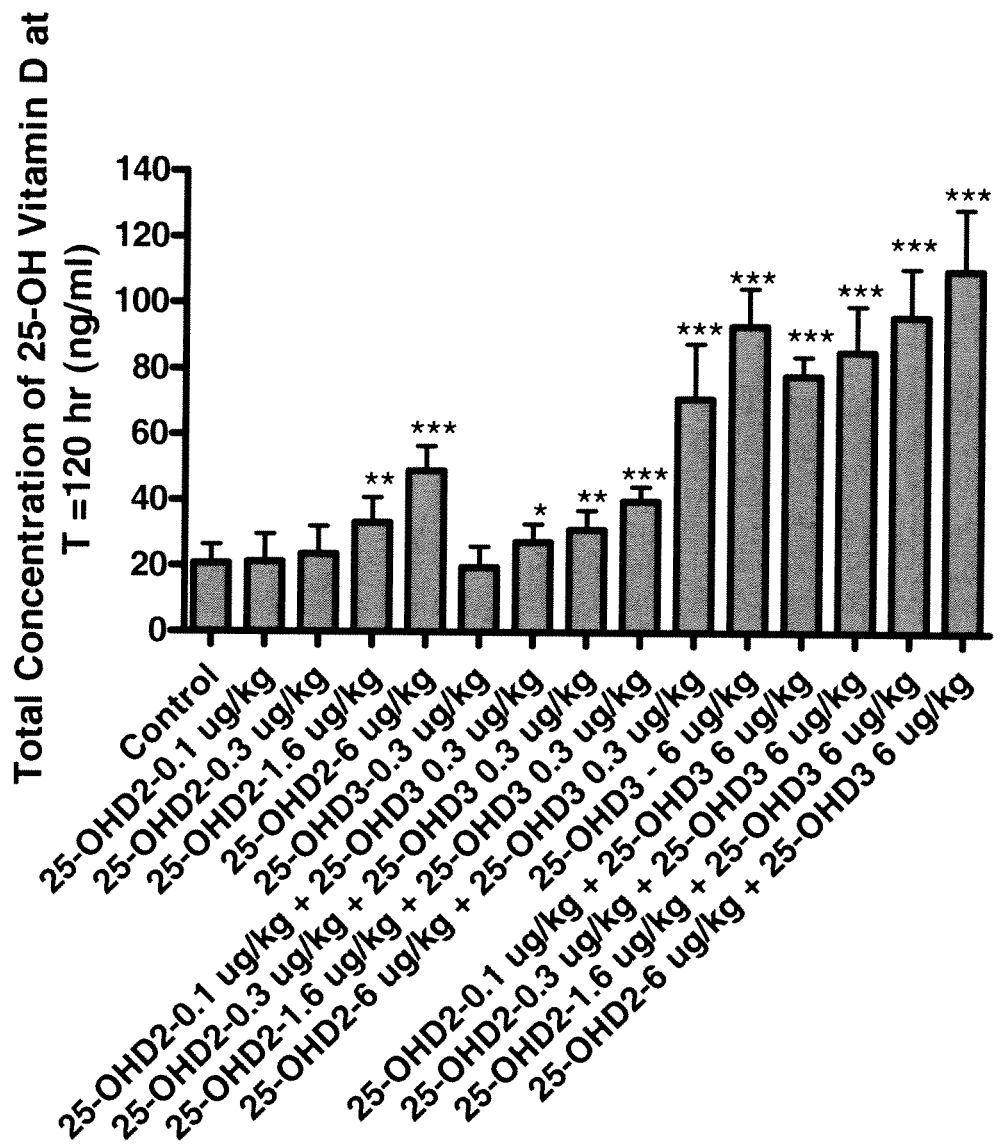
FIG. 1 shows the results of analysis of total 25-hydroxyvitamin D levels in rats administered various combinations of 25-hydroxyvitamin $D_2$ and 25-hydroxyvitamin $D_3$.

The present invention relates to a method for dosing a subject, an animal or a human patient, in need of Vitamin D supplementation with sufficient 25-hydroxyvitamin $D_2$ along with 25-hydroxyvitamin $D_3$ in a combination to effectively and safely restore blood 25-hydroxyvitamin D levels to optimal levels (defined for human subjects and patients as >30 ng/mL 25-hydroxyvitamin D), to maintain blood 25-hydroxyvitamin D levels at such optimal levels, to prevent a drop in blood 25-hydroxyvitamin D to suboptimal levels, and to prevent or treat secondary hyperparathyroidism.

The methods, compositions and kits of the present invention involve reduction or elimination of toxicity associated with administration of one or more vitamin $D_3$ supplements, by co-administration of one or more vitamin $D_2$ supplements. Co-administration of a vitamin $D_2$ supplement along with a vitamin $D_3$ supplement may result in reduced induction of catabolic enzymes such as CYP24, and therefore result in a more effective elevation in serum levels of total 25-hydroxyvitamin D than administration of either alone. Advantageously, the ratio of vitamin $D_3$ supplement to vitamin $D_3$ supplement is at least 1:1, 1.5:1, 2:1, 3:1, 5:1, 6:1, 7:1, 8:1, 9:1, 10:1, 15:1, 20:1, 30:1, 40:1, 50:1, 60:1, 75:1, 100:1 or more, based on the observation that 25-hydroxyvitamin $D_2$ appears to be catabolized more readily to 24,25-dihydroxyvitamin $D_2$ while the 25-hydroxyvitamin is metabolized catabolized more readily to the active 1,25-dihydroxyvitamin $D_3$ form.

Co-administration of a vitamin $D_3$ supplement and a vitamin $D_2$ supplement may permit administration of the vitamin $D_3$ supplement in amounts that would otherwise be considered close to, at or above the upper limit for chronic administration for no adverse effect, or its equivalent (divided into once, twice or three times weekly dosages) of more than approximately 1 μg/kg/day (based on the UL) of vitamin $D_3$, or the equivalent (divided into once, twice or three times weekly dosages) of more than 2-6 μg/kg/day of 25-hydroxyvitamin $D_3$, or the equivalent (divided into once, twice or three times weekly dosages) of more than 0.01 to 0.02 μg/kg/day of 1,25-dihydroxyvitamin $D_3$. Thus, unit dosage forms containing greater than 50 μg of vitamin $D_3$, greater than 50 μg of 25-hydroxyvitamin $D_3$, or greater than 1 μg of 1,25-dihydroxyvitamin $D_3$ are contemplated.

As used herein, the following definitions may be useful in aiding the skilled practitioner in understanding the invention:

The term "co-administration" when used with respect to a vitamin $D_2$ supplement or a vitamin $D_3$ supplement means that the two agents are administered in a manner that permits them both to exert their respective pharmacological effects during an overlapping period of time. The agents may be administered in the same formulation or in different formulations, at the same time or at different times, by the same route or by different routes. For example, co-administration may involve administration of a vitamin $D_3$ supplement at a time, e.g. within 6 hours, 8 hours, 12 hours, 24 hours (1 day), or 2 days, following the administration of a vitamin $D_2$ supplement when either the vitamin $D_2$ supplement or at least one or all metabolic products are detectable in serum. Alternatively, co-administration may involve administration of a vitamin $D_2$ supplement at a time, e.g. within 6 hours, 8 hours, 12 hours, 24 hours (1 day), or 2 days, following the administration of a vitamin $D_3$ supplement when either the vitamin $D_3$ supplement or at least one or all metabolic products are detectable in serum. In another embodiment, the patient may be given general instructions to take the vitamin $D_3$ supplement one, two or three times per week and the vitamin $D_2$ supplement one, two or three times per week, so long as each vitamin $D_2$ supplement and vitamin $D_3$ supplement is taken at least once (or twice or three times) per week.

The term "therapeutically effective amount" depends on the patient's condition and is an amount effective to achieve a desired clinical effect, e.g. to maintain a laboratory test value within the normal range or the recommended range for that patient's condition, or an amount effective to reduce the occurrence or severity of a clinical sign or symptom of disease. In some embodiments, a therapeutically effective amount is an amount effective on average to maintain serum 25-hydroxyvitamin D levels or 25-hydroxyvitamin $D_3$ levels at about 30 ng/mL (equivalent to about 75 nmol/L) or higher. Such levels may be maintained for an extended period, for example at least one month, at least three months, at least six months, nine months, one year, or longer. In other embodiments, a therapeutically effective amount is an amount effective on average to achieve at least a 15%, 20%, 25% or 30% reduction in serum parathyroid hormone levels (iPTH) from baseline levels without treatment. In yet other embodiments, a therapeutically effective amount is an amount effective on average to reach CKD stage-specific iPTH target ranges which for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1). When used in reference to an amount of a vitamin $D_3$ supplement, "therapeutically effective" can refer either to the effective amount of vitamin $D_3$ supplement when administered alone, or to the effective amount of vitamin $D_3$ supplement when administered in combination with a vitamin $D_2$ supplement.

As used herein, the term "Vitamin toxicity" is meant to refer to the adverse effects suffered from excessive administration of 25-hydroxyvitamin D and excessively elevated 25-hydroxyvitamin D blood levels, including nausea, vomiting, polyuria, hypercalciuria, hypercalcemia, and hyperphosphatemia. In some embodiments, toxicity is manifested by serum calcium rising above 10.2 mg/dL, and/or serum phosphorus rising above 4.6 mg/dL, and/or serum calcium× phosphorus product rising above 55, and/or urine calcium: creatinine ratio rising above 300 mg/24 hours.

"Vitamin D insufficiency and deficiency" is generally defined as having serum 25-hydroxyvitamin D levels below 30 ng/mL (equivalent to about 75 nmol/L) (National Kidney Foundation guidelines, NKF, Am. J. Kidney Dis. 42:S1-S202 (2003), incorporated herein by reference).

Unless indicated otherwise, "25-hydroxyvitamin $D_2$/25-hydroxyvitamin $D_3$" as used herein is intended to encompass 25-hydroxyvitamin $D_2$, 25-hydroxyvitamin $D_3$, or a combination thereof.

Unless indicated otherwise, "25-hydroxyvitamin D" is intended to refer to 25-hydroxyvitamin $D_2$ and 25-hydroxyvitamin $D_3$ collectively. For example, an assayed blood level of 25-hydroxyvitamin D will include both 25-hydroxyvitamin $D_2$ and 25-hydroxyvitamin $D_3$, if present.

The term "vitamin $D_2$ supplement" as used herein refers to a precursor, analog or derivative of ergocalciferol, 25-hydroxyvitamin $D_2$ or 1,25-dihydroxyvitamin $D_2$ that retains the ability to reduce vitamin D toxicity associated with administration of a vitamin $D_3$ supplement.

The term "vitamin $D_3$ supplement" as used herein refers to a precursor, analog or derivative of vitamin $D_3$ (cholecalciferol), 25-hydroxyvitamin $D_3$, or 1α,25-dihydroxyvitamin $D_3$, including, 1α-hydroxyvitamin $D_3$, that activates the vitamin D receptor or that can be metabolically converted in a human to a compound that activates the vitamin D receptor.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

The Food and Nutrition Board of the Institute of Medicine has determined there is insufficient scientific data to establish a Recommended Dietary Allowance (RDA) for vitamin D. Instead, the recommended intake is given as an Adequate Intake (AI), which represents the daily vitamin D intake that should maintain bone health and normal calcium metabolism in healthy people. AIs are generally set to meet or exceed the amount needed to prevent Vitamin D deficiency rickets or osteomalacia (or ≥11 ng/mL) in nearly all members of a specific age and gender group. AI for vitamin D can be listed as either micrograms (μg) or International Units (IU). The biological activity of 1 μg vitamin D is set as equal to 40 IUs. AIs for vitamin D for infants, children and adults are shown below in Table 1.

TABLE 1

| Age | Children (μg/day) | Men (μg/day) | Women (μg/day) | Pregnancy (μg/day) | Lactation (μg/day) |
|---|---|---|---|---|---|
| Birth to 13 years | 5 (=200 IU) | | | | |

TABLE 1-continued

| Age | Children (µg/day) | Men (µg/day) | Women (µg/day) | Pregnancy (µg/day) | Lactation (µg/day) |
|---|---|---|---|---|---|
| 14 to 18 years | | 5 (=200 IU) | 5 (=200 IU) | 5 (=200 IU) | 5 (=200 IU) |
| 19 to 50 years | | 5 (=200 IU) | 5 (=200 IU) | 5 (=200 IU) | 5 (=200 IU) |
| 51 to 70 years | | 10 (=400 IU) | 10 (=400 IU) | | |
| 71+ years | | 15 (=600 IU) | 15 (=600 IU) | | |

The Food and Nutrition Board of the Institute of Medicine has set the tolerable upper intake level (UL) for vitamin D at 25 µg (1,000 IU) for infants up to 12 months of age and 50 µg (2,000 IU) for children, adults, pregnant, and lactating women. Generally, ULs are set at the maximum daily intake unlikely to result in adverse health effects for vitamin D. Long term intakes above the UL may increase the risk of adverse health effects. ULs for vitamin D for infants, children and adults are shown below in Table 2.

TABLE 2

| Age | Men (µg/day) | Women (µg/day) | Pregnancy (µg/day) | Lactation (µg/day) |
|---|---|---|---|---|
| 0 to 12 months | 25 (=1,000 IU) | 25 (=1,000 IU) | | |
| 1 to 13 years | 50 (=2,000 IU) | 50 (=2,000 IU) | | |
| 14 to 18 years | 50 (=2,000 IU) | 50 (=2,000 IU) | 50 (=2,000 IU) | 50 (=2,000 IU) |
| 19+ years | 50 (=2,000 IU) | 50 (=2,000 IU) | 50 (=2,000 IU) | 50 (=2,000 IU) |

Other reports indicate that 95 µg/day (=3800 IU) is the lowest dose at which an adverse effect is observed.

The compositions, methods and kits of the invention are useful for treating any subject in need of vitamin D supplementation, either prophylactically to prevent vitamin D insufficiency or deficiency, or therapeutically to replete low serum vitamin 25(OH)D levels to normal range or above. The compositions and methods of the invention are also useful for preventing or treating secondary hyperparathyroidism resulting from low vitamin D levels. In general, serum 25(OH)D values less than 5 ng/mL indicate severe deficiency associated with rickets and osteomalacia. Although 30 ng/mL has been suggested as the low end of the normal range, more recent research suggests that PTH levels and calcium absorption are not optimized until serum total 25(OH)D levels reach approximately 40 ng/mL. [See also Vieth, R. Prog Biophys Mol Biol. 2006 September; 92(1): 26-32.] The term "subject" as used herein includes humans, mammals (e.g., dogs, cats, rodents, sheep, horses, cows, goats), veterinary animals and zoo animals.

Patients in need of vitamin D supplementation include healthy subjects and subjects at risk for vitamin D insufficiency or deficiency, for example, subjects with stage 1, 2, 3, 4 or 5 chronic kidney disease; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D in skin during exposure to sunlight and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with an Sun Protection Factor (SPF) of 8 reduces production of vitamin D by 95%, and higher SPFs may further reduce cutaneous vitamin D production); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin: subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis and/or postmenopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D. Optionally excluded from the methods of the invention are therapeutic treatment of subjects suffering from renal osteodystrophy (including osteomalacia and osteitis fibrosa cystica).

In other aspects, the compositions and methods of the invention are useful for prophylactic or therapeutic treatment of vitamin D-responsive diseases, i.e., diseases where vitamin D, 25(OH)D or active vitamin D (e.g., 1, 25(OH)$_2$D) prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25(OH)$_2$D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease (PKD), polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

The invention includes compositions comprising oral, intravenous and topical formulations of 25-hydroxyvitamin $D_2$ and 25-hydroxyvitamin $D_3$ and methods of administering such formulations to treat 25-hydroxyvitamin D insufficiency and deficiency without causing serious side effects associated with Vitamin D supplementation, namely Vitamin D toxicity.

The compositions of the present invention comprise highly stable pharmaceutical formulations into which 25-hydroxyvitamin $D_2$ and 25-hydroxyvitamin $D_3$ is incorporated for convenient daily oral administration. The disclosed compositions produce sustained blood levels of 25-hydroxyvitamin D with dual unexpected benefits with continued regular administration over a prolonged period of time of unsurpassed effectiveness in restoring blood 25-hydroxyvitamin D to optimal levels, and unsurpassed safety relative to heretofore known formulations of Vitamin D or 25-hydroxyvitamin D.

In another embodiment of the invention, sterile, isotonic formulations of 25-hydroxyvitamin $D_2$ combined with 25-hydroxyvitamin $D_3$ may be prepared which are suitable for intravenous administration. Such formulations are prepared by dissolving 25-hydroxyvitamin $D_2$ and 25-hydroxyvitamin $D_3$ in absolute ethanol, propylene glycol or other suitable solvents, and combining the resulting solutions with surfactants, salts and preservatives in appropriate volumes of water for injection. Such formulations can be administered immediately, or slowly from syringes via heparin locks or by addition to larger volumes of sterile solutions (e.g., saline solution) being steadily infused over time.

The dosage forms may also contain adjuvants, such as preserving or stabilizing adjuvants. They may also contain other therapeutically valuable substances or may contain more than one of the compounds specified herein and in the claims in admixture.

Advantageously, combinations of a vitamin $D_2$ supplement and a vitamin $D_3$ supplement together with other therapeutic agents can be orally or intravenously administered in accordance with the above described embodiments in dosage amounts of from 1 to 200 mcg per day, with the preferred dosage total amounts from 5 to 100 mcg per day. If the compounds of the present invention are administered in combination with other therapeutic agents, the proportions of each of the compounds in the combination being administered will be dependent on the particular disease state being addressed. For example, one may choose to orally administer the vitamin $D_2$ supplement and vitamin $D_3$ supplement with one or more calcium salts (intended as a calcium supplement or dietary phosphate binder), bisphosphonates, calcimimetics, nicotinic acid, iron, phosphate binders, active Vitamin D sterols, glycemic and hypertension control agents, and various antineoplastic agents. In addition, one may choose to intravenously administer 25-hydroxyvitamin $D_2$ and 25-hydroxyvitamin $D_3$, or 25-hydroxyvitamin $D_2$ and cholecalciferol, or 25-hydroxyvitamin $D_3$ and ergocalciferol, with active Vitamin D sterols, glycemic and hypertension control agents, and various antineoplastic agents. In practice, higher doses of the compounds of the present invention are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

The inclusion of a combination of a vitamin $D_3$ supplement and a vitamin $D_2$ supplement in the described delivery systems allows the resulting formulations to be useful in safely supporting both the Vitamin $D_3$ and Vitamin $D_2$ endocrine systems. Currently available oral Vitamin D supplements and the previously marketed oral formulation of 25-hydroxyvitamin $D_3$ have supported just one or the other system.

The present invention is further explained by the following examples which should not be construed by way of limiting the scope of the present invention.

EXAMPLE 1

Co-Administration of Various Combinations of 25-Hydroxyvitamin $D_3$ and 25-Hydroxyvitamin $D_2$ Alleviates Toxicity Observed by Treatment with 25-Hydroxyvitamin $D_3$ Alone To examine the reduction of toxicity associated with the co-administration of 25-hydroxyvitamin $D_3$ with 25-hydroxyvitamin $D_2$ compared to 25-hydroxyvitamin $D_3$ alone, 90 male Sprague-Dawley rats are treated intravenously for five consecutive days with various combinations of 25-hydroxyvitamin $D_3$ and 25-hydroxyvitamin $D_2$. One day prior to the initiation of the study, rats are randomly selected, assigned to groups and treated as follows in Table 3:

TABLE 3

| Group | 25-hydroxyvitamin $D_2$ dosing (µg/kg) | 25-hydroxyvitamin $D_3$ dosing (µg/kg) | Number of Animals/ Sex | Dose Volume (mL/kg) | Frequency of Dosing | Blood sampling time (hrs) |
|---|---|---|---|---|---|---|
| 1 | 0 | 0 | 6 males | 0.8 | once a day for 5 days, i.v | Pre dosing, 24 h (day 2) and 120 h (day 6) |
| 2 | 0.1 | 0 | | | | |
| 3 | 0.3 | 0 | | | | |

TABLE 3-continued

| Group | 25-hydroxyvitamin $D_2$ dosing (µg/kg) | 25-hydroxyvitamin $D_3$ dosing (µg/kg) | Number of Animals/ Sex | Dose Volume (mL/kg) | Frequency of Dosing | Blood sampling time (hrs) |
|---|---|---|---|---|---|---|
| 4 | 1.6 | 0 | | | | |
| 5 | 6 | 0 | | | | |
| 6 | 0 | 0.3 | | | | |
| 7 | 0.1 | 0.3 | | | | |
| 8 | 0.3 | 0.3 | | | | |
| 9 | 1.6 | 0.3 | | | | |
| 10 | 6 | 0.3 | | | | |
| 11 | 0 | 6 | | | | |
| 12 | 0.1 | 6 | | | | |
| 13 | 0.3 | 6 | | | | |
| 14 | 1.6 | 6 | | | | |
| 15 | 6 | 6 | | | | |

For each day's treatment of each animal, the appropriate material was administered i.v. Daily treatments were performed within a 3 hours window on each day. On the first day of treatment (pre-dose) and at 24 hours time points on day 2 before the second dose administration (0 being the time of the first injection), blood (~1 mL) was collected from the jugular vein catheter from animals in Group 1 to 15 into unpreserved tubes. The serum was separated out, transferred into new tubes that were immediately frozen at approximately −80° C. Prior to the sacrifice of all animals at 120 hours on Day 6 blood (~2 mL) was collected into unpreserved tubes from the jugular vein catheter from all animals. The serum was separated out, transferred into new tubes and immediately frozen at approximately −80° C. Also, on Day 6 at 120 hours (24 hours post last dosing), all animals were euthanized by carbon dioxide inhalation, total bleed was collected by cardiac puncture. Blood was placed into unpreserved (i.e. red-stoppered) tubes. The serum was separated, transferred in new tubes (1 mL aliquots) and immediately frozen at approximately −80° C. All animals were then subjected to necropsy. In order to avoid autolytic changes, the necropsy examination of the carcass was conducted as soon as possible. For each animal, the necropsy consisted of an external examination, including reference to all clinically recorded lesions, as well as internal "abbreviated" examinations.

The concentration of total 25-hydroxyvitamin D at 120 hours post initial dose was determined in serum samples using a high-performance liquid chromatographic method using tandem mass spectrometry detection. The method was utilized to determine the individual concentrations of 25-hydroxyvitamin $D_3$ and 25-hydroxyvitamin $D_2$ in serum and the total was determined as a sum of the concentrations. At 24 h post final dose, serum collected from animals was analyzed for changes in levels of 25-hydroxyvitamin $D_3$, 25-hydroxyvitamin $D_2$ and their metabolites.

CYP24 induction was measured in kidney as follows: One eighth (⅛) of kidney was sliced and homogenized for RNA isolation using the TRIzol method. After cDNA synthesis, the levels of Cyp24 mRNA were evaluated, and normalized to Gapdh mRNA, using a specific CYP24 probe by real time RT-PCR.

FIG. 1, 25-hydroxyvitamin D levels, shows the elevation in total serum 25-hydroxyvitamin D when rats are administered either 25-hydroxyvitamin $D_3$ either alone or in combination with the indicated dosing, daily for a period of 5 days.

Table 4, shown below, indicates observed findings upon gross necropsy of animals following the 5 day dosing study. Severe signs of toxicity (blood in the lungs) was observed only in the group of animals receiving the highest dose of 25-hydroxyvitamin $D_3$ (6 µg/kg) alone.

TABLE 4

| Group | 25-hydroxyvitamin $D_2$ (µg/kg) | 25-hydroxyvitamin $D_3$ (µg/kg) | Gross Necropsy Findings |
|---|---|---|---|
| 1 | 0 | 0 | None |
| 2 | 0.1 | 0 | None |
| 3 | 0.3 | 0 | None |
| 4 | 1.6 | 0 | None |
| 5 | 6 | 0 | None |
| 6 | 0 | 0.3 | None |
| 7 | 0.1 | 0.3 | None |
| 8 | 0.3 | 0.3 | None |
| 9 | 1.6 | 0.3 | None |
| 10 | 6 | 0.3 | None |
| 11 | 0 | 6 | 4/6 animals had blood in the lung |
| 12 | 0.1 | 6 | None |
| 13 | 0.3 | 6 | None |
| 14 | 1.6 | 6 | None |
| 15 | 6 | 6 | None |

Figure 2:
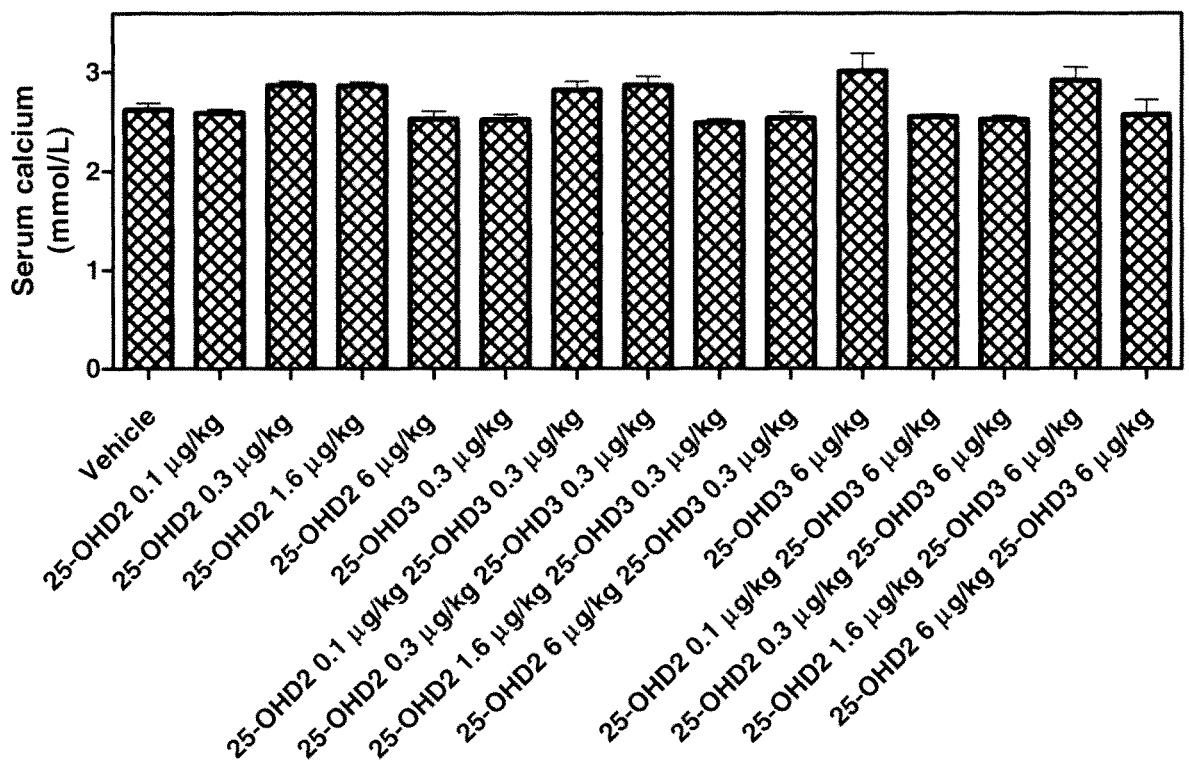
FIG. 2 shows the results of analysis of serum calcium levels in rats administered various combinations of 25-hydroxyvitamin $D_2$ and 25-hydroxyvitamin $D_3$.

FIG. 2, serum calcium levels, shows the highest achieved level of serum calcium was observed in the Group 11, which received 6 µg/kg 25-hydroxyvitamin $D_3$ alone. These animals also suffered from signs of toxicity upon gross necropsy. Toxicity was lessened or eliminated by co-administration of 25-hydroxyvitamin $D_2$, even when total 25-hydroxyvitamin D dosing levels exceeded 6 µg/kg.

The results of this study indicate that toxicity associated with 25-hydroxyvitamin $D_3$ dosing, including elevation in serum calcium, can be reduced or eliminated by co-administration of 25-hydroxyvitamin $D_2$. Even a small proportion (1:60) of added 25-hydroxyvitamin $D_2$ can significantly reduce elevations of serum calcium caused by 25-hydroxyvitamin $D_3$. In the most extreme example, animals administered 6 µg/kg 25-hydroxyvitamin $D_3$ over a 5 day treatment period showed hypercalcemia with 4 of 6 animals treated exhibiting blood in lung tissue upon necropsy. Surprisingly, if animals were co-administered 0.1 µg/kg 25-hydroxyvitamin $D_2$ with 6 µg/kg 25-hydroxyvitamin $D_3$, serum calcium levels approached normal and animals did not exhibit any signs of toxicity. The safety benefit was maintained even when the animals were administered a total amount of 25-hydroxyvitamin D that was double the amount of 25-hydroxyvitamin $D_3$ that induced toxicity (6 µg/kg/day 25-hydroxyvitamin $D_3$ and 6 µg/kg/day 25-hydroxyvitamin $D_2$). These studies demonstrate the utility of 25-hydroxyvitamin $D_2$ as a protective agent in 25-hydroxyvitamin $D_3$ therapy.

Figure 3:
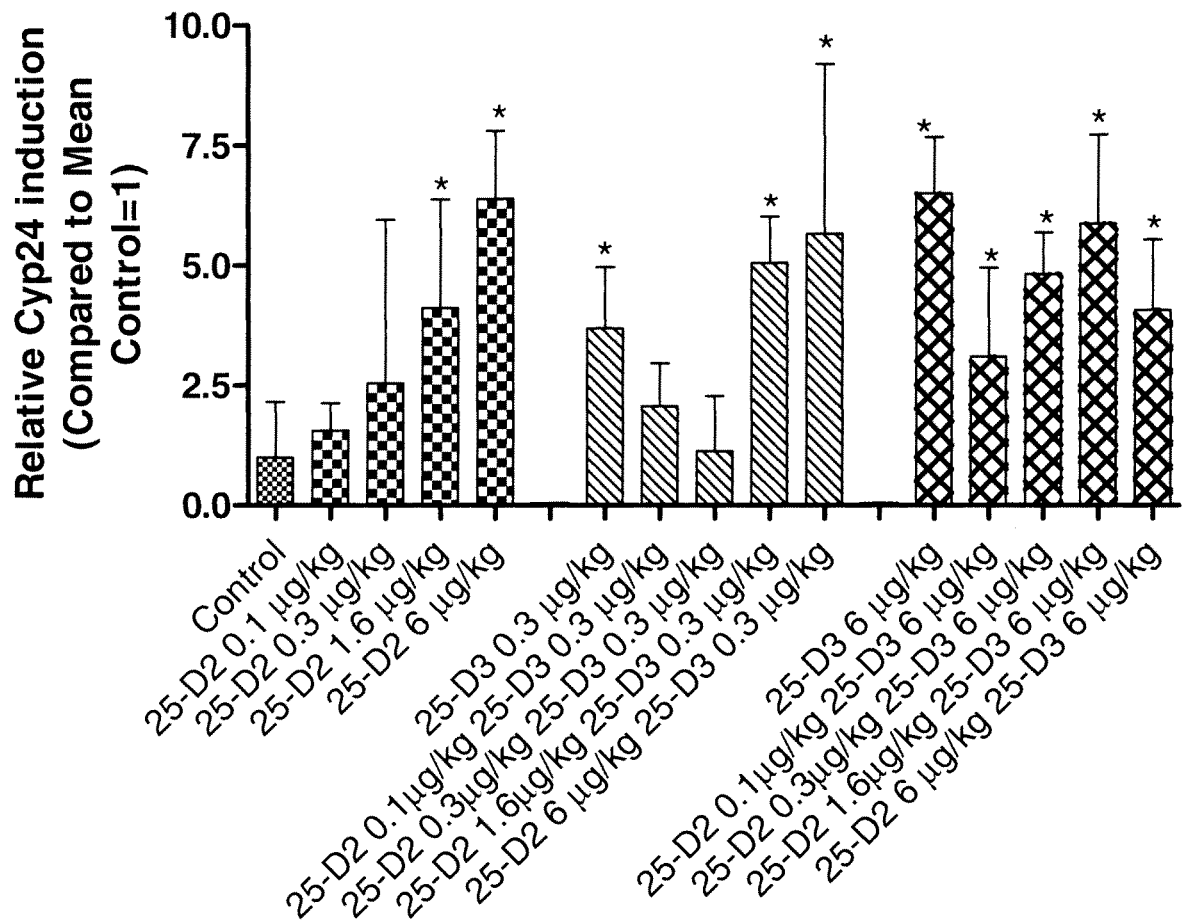
FIG. 3 shows the results of analysis of CYP24 levels in the kidney of rats administered various combinations of 25-hydroxyvitamin $D_2$ and 25-hydroxyvitamin $D_3$.
Figure 4:
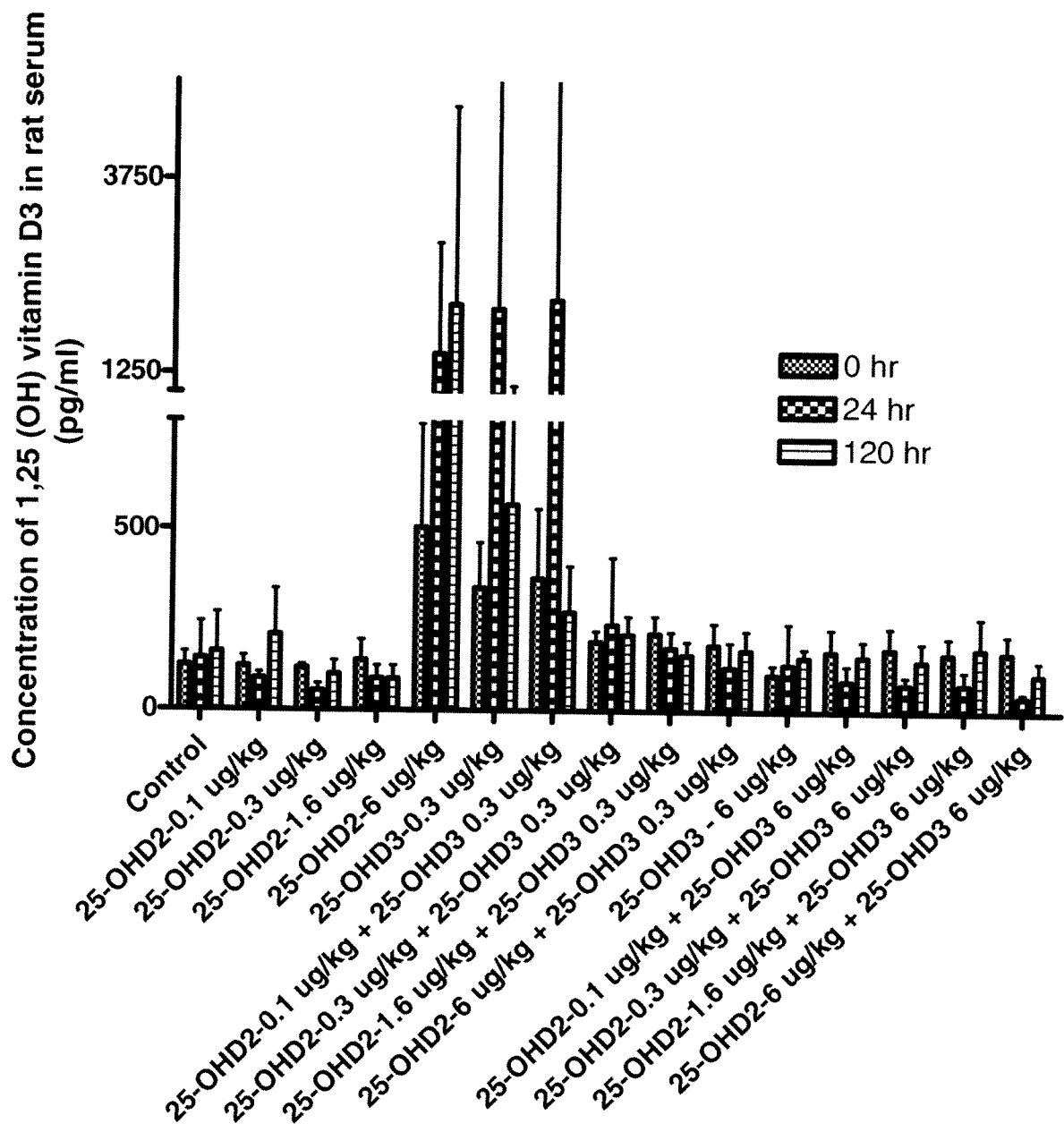
FIG. 4 shows the results of analysis of 1,25-dihydroxyvitamin $D_3$ levels in rats administered various combinations of 25-hydroxyvitamin $D_2$ and 25-hydroxyvitamin $D_3$.
Figure 5:
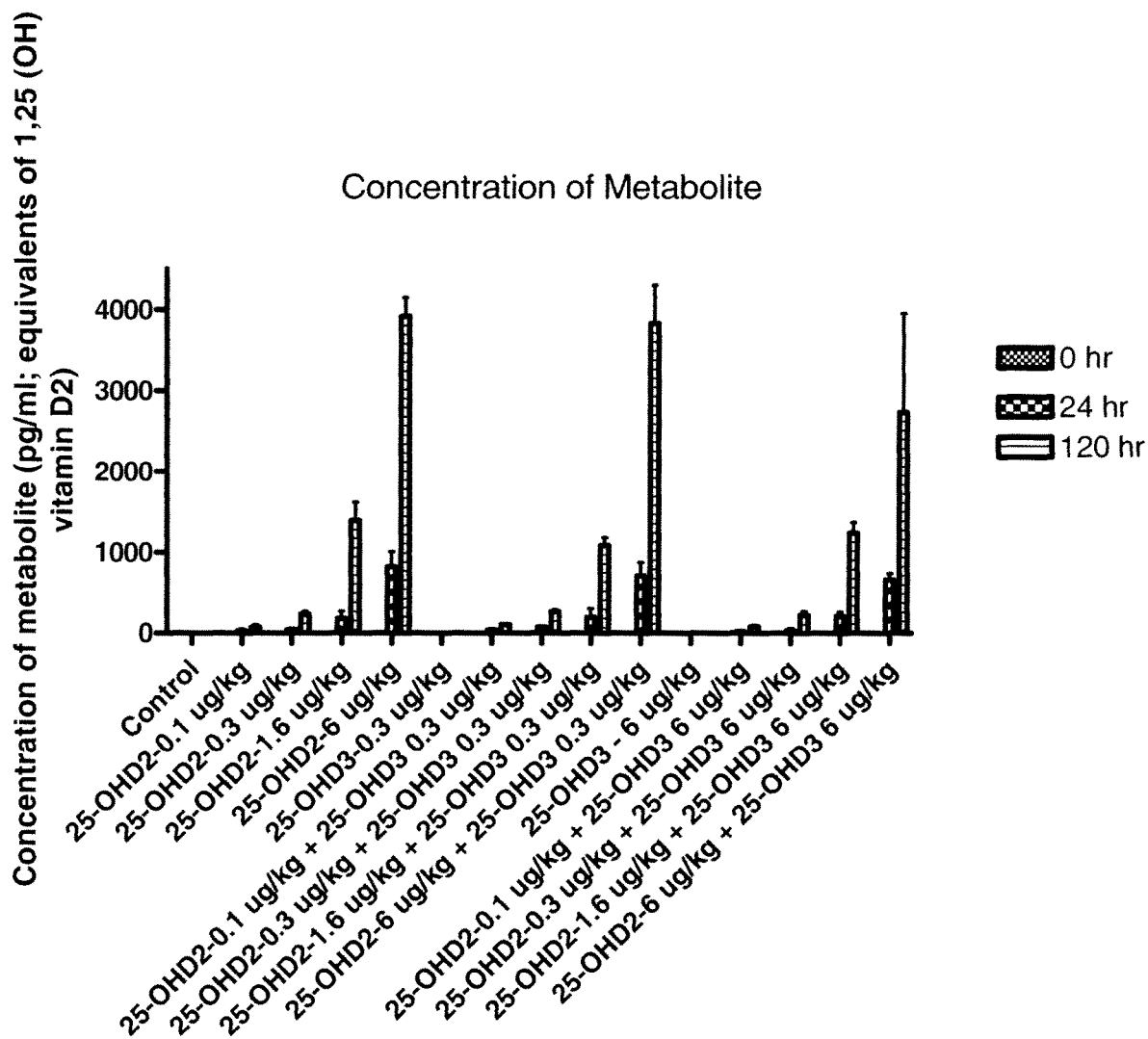
FIG. 5 shows the results of analysis of levels of a metabolite of 25-hydroxyvitamin $D_2$ in rats administered various combinations of 25-hydroxyvitamin $D_2$ and 25-hydroxyvitamin $D_3$.

The data in FIG. 3 indicate that the co-administration of 25-hydroxyvitamin $D_3$ and 25-hydroxyvitamin $D_2$ results in less upregulation of CYP24 compared to administration of 25-hydroxyvitamin $D_3$ alone. Thus, the data suggest that co-administration of 25-hydroxyvitamin $D_3$ along with 25-hydroxyvitamin $D_2$ can more effectively elevate serum levels of 25-hydroxyvitamin D than administration of either alone.

EXAMPLE 2

Another Study of Co-Administration of Various Combinations of 25-Hydroxyvitamin $D_3$ And 25-Hydroxyvitamin $D_2$ Alleviates Toxicity Observed by Treatment with 25-Hydroxyvitamin $D_3$ Alone.

Another study was carried out to assess the effects of co-administration of 25-hydroxyvitamin D with 25-hydroxyvitamin $D_2$ compared to 25-hydroxyvitamin $D_3$ alone on 102 male Sprague-Dawley rats. Rats about 3 days in age, about 175-250 g in weight, were divided into groups of six males each. The groups were administered various combinations of 25-hydroxyvitamin $D_3$ and 25-hydroxyvitamin $D_2$ intravenously (or the same volume of control vehicle) once daily via the jugular vein catheter, for five consecutive days, according to Table 5 below.

Example 1. For example, doses of 4 μg/kg or 8 μg/kg 25-hydroxyvitamin $D_3$ alone resulted in hypercalcemia, while a combined dose of 8 μg/kg and 8 μg/kg 25-hydroxyvitamin $D_3$ with 25-hydroxyvitamin $D_2$ resulted in normal serum calcium levels, indicating that the inclusion of the 25-hydroxyvitamin $D_2$ was able to alleviate the toxicity associated with the 25-hydroxyvitamin $D_3$.

EXAMPLE 3

Efficacy and Safety Study in Advanced Prostate Cancer Patients Treated with High-Dose Formulations of Vitamin D Hormone.

The efficacy and safety of an oral preparation of 25-hydroxyvitamin $D_2$ is examined in a 3-month study of patients with advanced prostate cancer being treated with high-dose calcitriol once per week. For this study, 25-hydroxyvitamin $D_2$ was formulated in soft-gelatin capsules. Forty patients with advanced prostate cancer undergoing treatment with high-dose calcitriol and Docetaxel were divided into two equal groups. Along with weekly calcitriol doses, group #1 receives between 2-20 mcg 25-hydroxyvitamin $D_2$, while group #2 receives placebo. Prior to enrolling, all subjects provide two fasting morning blood samples, separated by at least one week, to establish pre-treatment baseline values of

TABLE 5

| Treatment Group (μg/kg) | Number of Animals/ Gender | Rat | Dose Volume (mL/kg) | Frequency of Dosing |
|---|---|---|---|---|
| 1. Vehicle | 6 males | Normal with a jugular vein catheter | 0.8 | once a day for 5 days, i.v. via the jugular vein catheter |
| 2. 25-hydroxyvitamin $D_3$ (4) | | | | |
| 3. 25-hydroxyvitamin $D_3$ (8) | | | | |
| 4. 25-hydroxyvitamin $D_3$ (4) + 25-hydroxyvitamin $D_2$ (0.2) | | | | |
| 5. 25-hydroxyvitamin $D_3$ (4) + 25-hydroxyvitamin $D_2$ (0.4) | | | | |
| 6. 25-hydroxyvitamin $D_3$ (4) + 25-hydroxyvitamin $D_2$ (0.8) | | | | |
| 7. 25-hydroxyvitamin $D_3$ (4) + 25-hydroxyvitamin $D_2$ (1.6) | | | | |
| 8. 25-hydroxyvitamin $D_3$ (4) + 25-hydroxyvitamin $D_2$ (2.4) | | | | |
| 9. 25-hydroxyvitamin $D_3$ (4) + 25-hydroxyvitamin $D_2$ (3) | | | | |
| 10. 25-hydroxyvitamin $D_3$ (4) + 25-hydroxyvitamin $D_2$ (4) | | | | |
| 11. 25-hydroxyvitamin $D_3$ (8) + 25-hydroxyvitamin $D_2$ (0.4) | | | | |
| 12. 25-hydroxyvitamin $D_3$ (8) + 25-hydroxyvitamin $D_2$ (0.8) | | | | |
| 13. 25-hydroxyvitamin $D_3$ (8) + 25-hydroxyvitamin $D_2$ (1.6) | | | | |
| 14. 25-hydroxyvitamin $D_3$ (8) + 25-hydroxyvitamin $D_2$ (3.2) | | | | |
| 15. 25-hydroxyvitamin $D_3$ (8) + 25-hydroxyvitamin $D_2$ (4.8) | | | | |
| 16. 25-hydroxyvitamin $D_3$ (8) + 25-hydroxyvitamin $D_2$ (6) | | | | |
| 17. 25-hydroxyvitamin $D_3$ (8) + 25-hydroxyvitamin $D_2$ (8) | | | | |

Dosing was carried out at similar times each day, within a three hour window of the time of last dose. Blood was collected at day 0 (the first day of treatment) for analysis, and animals were monitored twice daily. Animals from all groups were euthanized on day 5, 24 hours after the last dose, and blood was collected by cardiac puncture. All rats were subjected to an abbreviated necropsy.

Figure 6:
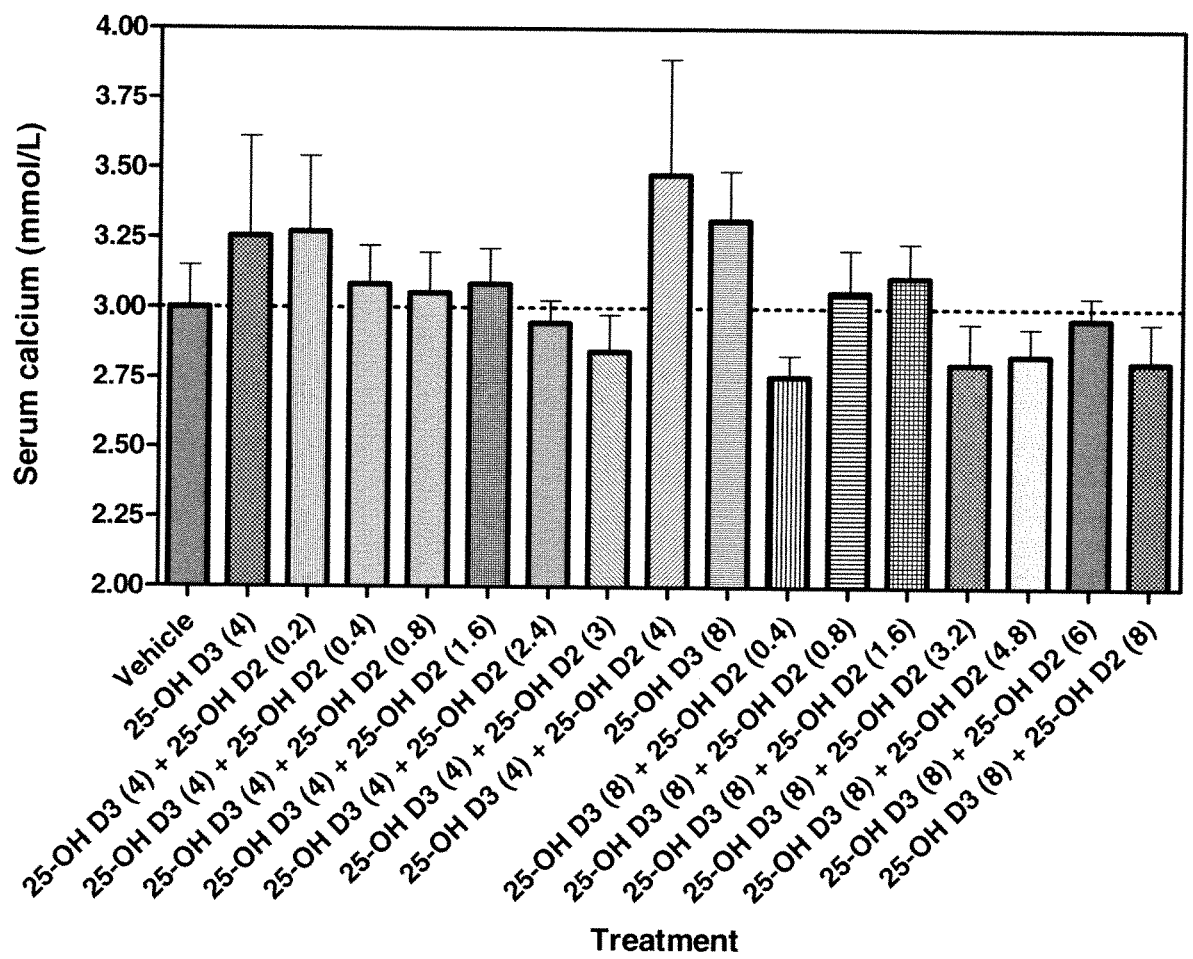
FIG. 6 shows the results in a different study of analysis of serum calcium levels in rats administered various combinations of 25-hydroxyvitamin $D_2$ and 25-hydroxyvitamin $D_3$.

Serum calcium levels of the rats at day 5 of treatment are displayed in FIG. 6 and confirm the data described above for serum calcium, plasma intact PTH, and serum 25-hydroxyvitamin D. Additional fasting blood samples and 24-hour urine collections are obtained from each subject 24 h following the administration of the weekly administration of calcitriol for determination of serum calcium and serum 25-hydroxyvitamin D. Throughout the study, all subjects adhere to a daily intake of approximately 1,000 to 1,500 mg of elemental calcium (from self-selected diets and calcium supplements, as needed) under the ongoing guidance of a dietician. At the conclusion of the study, the laboratory data are analyzed by treatment group and by test formulation after appropriate correction for baseline values. All groups are expected to have comparable mean baseline values for serum 25-hydroxyvitamin D (range: 10.7 to 20.9 ng/mL) and serum calcium (range: 8.72 to 9.31 mg/dL). Increased laboratory mean values for serum calcium are expected to be observed in the placebo (control) group over the course of the study, however, much lower changes in serum calcium levels (e.g., no change or reduced increase) are expected to be observed in the treatment group. Subjects in the treatment group receiving 25-hydroxyvitamin $D_2$ are expected to exhibit progressively increasing serum 25-hydroxyvitamin D levels during the first 2-3 months of dosing, reaching steady state levels thereafter. Episodes of hypercalcemia, defined as serum calcium above 10.2 mg/dL, are expected to be more frequently observed in the placebo group than in the treatment group. Data from this study are expected to demonstrate that elevation in serum calcium in the treatment of prostate cancer patients with high-dose calcitriol can be controlled or alleviated altogether by adding 25-hydroxyvitamin $D_2$ to the treatment regimen.

EXAMPLE 4

Efficacy and Safety Study in End-Stage Renal Disease Patients Exhibiting Vitamin D Deficiency The efficacy and safety of an intravenous 25-hydroxyvitamin $D_3$/25-hydroxyvitamin $D_2$ combination in restoring serum 25-hydroxyvitamin D to optimal levels (>30 ng/mL) are examined in a 3-month study of patients with end-stage renal disease (ESRD) requiring regular hemodialysis and diagnosed with Vitamin D insufficiency. The formulations examined in this study are aqueous isotonic and sterile solutions containing either 20 mcg of 25-hydroxyvitamin $D_3$ alone (test preparation #1) or in combination with 10 mcg 25-hydroxyvitamin $D_2$ (test preparation #2). A total of 75 healthy Caucasian, Asian, Hispanic and African-American subjects participate in this study, all of whom are at least 4-months on regular hemodialysis and have serum 25-hydroxyvitamin D levels below 15 ng/mL. Prior to enrolling, all subjects provide two fasting morning blood samples, separated by at least one week, to establish pre-treatment baseline values of serum calcium, plasma intact PTH, and serum 25-hydroxyvitamin D. On the morning of Day 1, the subjects are randomly assigned to one of three treatment groups, and they begin thrice weekly dosing with the test preparation #1 or #2, or with a matching placebo. All dosing occurs during regularly scheduled hemodialysis sessions and is accomplished by gradual injection (over a period of 1 to 5 minutes) into the blood exiting from the hemodialysis machine. Additional fasting blood samples and 24-hour urine collections are obtained from each subject at quarterly intervals for determination of serum calcium, plasma intact PTH and serum 25-hydroxyvitamin D. Throughout the study, all subjects adhere to a daily intake of approximately 1,000 to 1,500 mg of elemental calcium (from self-selected diets and calcium supplements, as needed) under the ongoing guidance of a dietician. At the conclusion of the study, the laboratory data are analyzed by treatment group and by test formulation after appropriate correction for baseline values. All groups are expected to have comparable mean baseline values for serum 25-hydroxyvitamin D (range: 10.7 to 11.9 ng/mL), plasma intact PTH (range: 45.3 to 52.1 pg/mL) and serum calcium (range: 8.72 to 9.31 mg/dL). No significant changes in any of the laboratory mean values are expected to be observed in the placebo (control) group over the course of the study. Subjects in the both treatment groups receiving 25-hydroxyvitamin $D_3$ alone or the 25-hydroxyvitamin $D_3$/25-hydroxyvitamin combination are expected to exhibit progressively increasing serum 25-hydroxyvitamin D levels during the first 3 months of dosing, reaching steady state levels thereafter. Mean serum calcium is expected to increase significantly from baseline in the treatment group receiving 25-hydroxyvitamin $D_3$, and is expected to be significantly higher than those observed in the placebo group. Subjects in the treatment group receiving the 25-hydroxyvitamin $D_3$/25-hydroxyvitamin $D_2$ combination are expected to exhibit serum calcium levels significantly lower than those observed for the 25-hydroxyvitamin $D_3$-alone treatment group but not significantly different than those observed in the placebo group. Episodes of hypercalcemia, defined as serum calcium above 10.2 mg/dL, are expected to be more frequently observed in the treatment group receiving only 25-hydroxyvitamin $D_3$. Data from this study are expected to demonstrate that the intravenous formulation of 25-hydroxyvitamin $D_3$ combined with 25-hydroxyvitamin $D_2$ is equally or more effective at increasing serum 25-hydroxyvitamin D than that comprised of 25-hydroxyvitamin $D_3$ alone without causing significant elevation of serum calcium levels. The conclusions from this study are expected to support that combining 25-hydroxyvitamin $D_3$ and 25-hydroxyvitamin $D_2$ is the safe way to raise serum 25-hydroxyvitamin D levels.

All patents, publications and references cited herein are hereby fully incorporated by reference. In case of conflict between the present disclosure and incorporated patents, publications and references, the present disclosure should control.

What is claimed is:

1. A method of maintaining or elevating serum levels of 25-hydroxyvitamin D, comprising co-administering to a subject 25-hydroxyvitamin $D_3$ and 25-hydroxyvitamin $D_2$, wherein the weight or molar ratio of 25-hydroxyvitamin $D_3$ to 25-hydroxyvitamin $D_2$ is at least 1.5:1.

2. The method of claim 1, wherein said-co-administering comprises administering a therapeutically effective amount of the 25-hydroxyvitamin $D_3$ and administering the 25-hydroxyvitamin $D_2$ in an amount effective to reduce vitamin D toxicity.

3. The method according to claim 1, wherein the weight or molar ratio of 25-hydroxyvitamin $D_3$ to 25-hydroxyvitamin $D_2$ is in a range of 100:1 to 2:1.

4. The method according to claim 1, wherein the ratio of 25-hydroxyvitamin $D_3$ to 25-hydroxyvitamin $D_2$ is at least 2:1.

5. The method according to claim 1, comprising administering 25-hydroxyvitamin $D_3$ in an amount greater than 2 μg/kg/day.

6. The method according to claim 1, comprising administering the 25-hydroxyvitamin $D_3$ and the 25-hydroxyvitamin $D_2$ within 6 hours of each other.

7. The method according to claim 6, comprising first administering the 25-hydroxyvitamin $D_3$ and then administering the 25-hydroxyvitamin $D_2$ at a time when either the 25-hydroxyvitamin $D_3$ or a metabolic product thereof is detectable in serum.

8. The method according to claim 6, comprising first administering the 25-hydroxyvitamin $D_2$ and then administering the 25-hydroxyvitamin $D_3$ at a time when either the 25-hydroxyvitamin $D_2$ or a metabolic product thereof is detectable in serum.

9. The method according to claim 1, comprising administering said 25-hydroxyvitamin $D_3$ and 25-hydroxyvitamin $D_2$ to a patient diagnosed with vitamin D insufficiency and/or deficiency.

10. The method according to claim 1, comprising administering said 25-hydroxyvitamin $D_3$ and 25-hydroxyvitamin $D_2$ in amount sufficient to raise and/or maintain the serum 25-hydroxyvitamin D level of the subject to at least 30 ng/mL.

11. The method according to claim 1, wherein the subject is a human.

12. A method of vitamin D supplementation, comprising co-administering a vitamin $D_3$ supplement which is 25-hydroxyvitamin $D_3$ or 1,25-dihydroxyvitamin $D_3$, and a vitamin $D_2$ supplement which is 25-hydroxyvitamin $D_2$ or 1,25-dihydroxyvitamin $D_2$, and wherein the weight or molar ratio of 25-hydroxyvitamin $D_3$ or 1,25-dihydroxyvitamin $D_3$ to 25-hydroxyvitamin $D_2$ or 1,25-dihydroxyvitamin $D_2$ is at least 1.5:1 not 1:1.

13. The method according to claim 11, wherein the subject has secondary hyperparathyroidism.

14. The method according to claim 1, wherein the subject is a mammal.

15. The method according to claim 1, wherein the administration of one or both of 25-hydroxyvitamin $D_3$ and 25-hydroxyvitamin $D_2$ is selected from oral, intravenous, topical, intraperitoneal and trans-dermal.

16. The method according to claim 15, wherein the administration of 25-hydroxyvitamin $D_3$ is oral.

17. The method according to claim 16, wherein the administration of 25-hydroxyvitamin $D_2$ is oral.

18. The method according to claim 15, wherein the administration of 25-hydroxyvitamin $D_3$ is intravenous.

19. The method according to claim 18, wherein the administration of 25-hydroxyvitamin $D_2$ is intravenous.

* * * * *

UNITED STATES PATENT AND TRADEMARK OFFICE
CERTIFICATE OF CORRECTION

| | | |
|---|---|---|
| PATENT NO. | : 11,752,158 B2 | Page 1 of 1 |
| APPLICATION NO. | : 12/597230 | |
| DATED | : September 12, 2023 | |
| INVENTOR(S) | : Petkovich et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this
Fifth Day of August, 2025

Coke Morgan Stewart
*Acting Director of the United States Patent and Trademark Office*